(12) United States Patent
Fissell et al.

(10) Patent No.: US 9,403,126 B2
(45) Date of Patent: Aug. 2, 2016

(54) ULTRAFILTRATION MEMBRANE, DEVICE, BIOARTIFICIAL ORGAN, AND RELATED METHODS

(75) Inventors: William H. Fissell, Brecksville, OH (US); Shuvo Roy, Shaker Heights, OH (US); Aaron Fleischman, Beachwood, OH (US); Kenneth G. Goldman, Olmsted Falls, OH (US)

(73) Assignees: THE REGENTS OF THE UNIVERSITY OF MICHIGAN, Ann Arbor, MI (US); THE CLEVELAND CLINIC FOUNDATION, Cleveland, OH (US)

( * ) Notice: Subject to any disclaimer, the term of this patent is extended or adjusted under 35 U.S.C. 154(b) by 1192 days.

(21) Appl. No.: 11/972,502

(22) Filed: Jan. 10, 2008

(65) Prior Publication Data
US 2009/0131858 A1    May 21, 2009

Related U.S. Application Data

(60) Provisional application No. 60/879,744, filed on Jan. 10, 2007.

(51) Int. Cl.
| | |
|---|---|
| *A61M 1/00* | (2006.01) |
| *B01D 61/14* | (2006.01) |
| *A61B 5/103* | (2006.01) |
| *B01D 61/18* | (2006.01) |
| *B01D 61/20* | (2006.01) |
| *B01D 67/00* | (2006.01) |

(52) U.S. Cl.
CPC ............. *B01D 61/145* (2013.01); *B01D 61/18* (2013.01); *B01D 61/20* (2013.01); *B01D 67/0034* (2013.01); *B01D 67/0062* (2013.01); *B01D 67/0088* (2013.01); *B01D 2313/243* (2013.01); *B01D 2321/22* (2013.01); *B01D 2325/028* (2013.01)

(58) Field of Classification Search
USPC ................................................ 210/243, 321.6
See application file for complete search history.

(56) References Cited

U.S. PATENT DOCUMENTS

| 4,797,211 A | 1/1989 | Ehrfeld |
| 4,923,608 A | 5/1990 | Flottmann |

(Continued)

FOREIGN PATENT DOCUMENTS

| WO | WO 89/01967 | 3/1989 |
| WO | WO 95/13860 | 5/1995 |

(Continued)

OTHER PUBLICATIONS

International Search Report, PCT/US08/50773, mailed May 20, 2008.

(Continued)

*Primary Examiner* — Dirk Bass
(74) *Attorney, Agent, or Firm* — Casimir Jones, S.C.

(57) ABSTRACT

The present invention relates to ultrafiltration. In particular, the present invention provides nanoporous membranes having pores for generating in vitro and in vivo ultrafiltrate, devices and bioartificial organs utilizing such nanoporous membranes, and related methods (e.g., diagnostic methods, research methods, drug screening). The present invention further provides nanoporous membranes configured to avoid protein fouling with, for example, a polyethylene glycol surface coating.

45 Claims, 19 Drawing Sheets

(56) References Cited

U.S. PATENT DOCUMENTS

| | | | |
|---|---|---|---|
| 5,543,046 A | 8/1996 | Van Rijn | |
| 5,549,674 A | 8/1996 | Humes | |
| 5,651,900 A | 7/1997 | Keller | |
| 5,686,289 A | 11/1997 | Humes | |
| 5,736,372 A | 4/1998 | Vacanti | |
| 5,753,014 A | 5/1998 | Van Rijn | |
| 5,759,830 A | 6/1998 | Vacanti | |
| 5,770,076 A | 6/1998 | Chu | |
| 5,770,193 A | 6/1998 | Vacanti | |
| 5,770,417 A | 6/1998 | Vacanti | |
| 5,776,748 A | 7/1998 | Singhvi | |
| 5,798,042 A | 8/1998 | Chu | |
| 5,843,741 A | 12/1998 | Wong | |
| 5,882,496 A | 3/1999 | Northrup | |
| 5,893,974 A | 4/1999 | Keller | |
| 5,938,923 A | 8/1999 | Tu | |
| 5,948,255 A | 9/1999 | Keller | |
| 5,976,826 A | 11/1999 | Singhvi | |
| 5,985,164 A | 11/1999 | Chu | |
| 5,985,328 A | 11/1999 | Chu | |
| 6,015,599 A | 1/2000 | Keller | |
| 6,017,390 A | 1/2000 | Charych | |
| 6,042,784 A | 3/2000 | Wamsiedler | |
| 6,044,981 A | 4/2000 | Chu | |
| 6,060,270 A | 5/2000 | Humes | |
| 6,107,102 A | 8/2000 | Ferrari | |
| 6,150,164 A | 11/2000 | Humes | |
| 6,180,239 B1 | 1/2001 | Whitesides | |
| 6,368,838 B1 | 4/2002 | Singhvi | |
| 6,368,877 B1 | 4/2002 | Zhang | |
| 6,405,066 B1 | 6/2002 | Essenpreis | |
| 6,410,320 B1 | 6/2002 | Humes | |
| 6,569,654 B2 | 5/2003 | Shastri | |
| 6,598,750 B2 | 7/2003 | Tai | |
| 7,048,856 B2 | 5/2006 | Fissell | |
| 7,332,330 B2 | 2/2008 | Humes | |
| 2004/0124147 A1* | 7/2004 | Fissell et al. | 210/650 |
| 2005/0263452 A1* | 12/2005 | Jacobson | 210/484 |
| 2006/0154361 A1 | 7/2006 | Wikswo | |
| 2006/0213836 A1 | 9/2006 | Fissell | |

FOREIGN PATENT DOCUMENTS

| | | |
|---|---|---|
| WO | WO 98/10267 | 3/1998 |
| WO | WO 98/13131 | 4/1998 |
| WO | WO 01/41905 | 6/2001 |

OTHER PUBLICATIONS

Bidaud, M., et al., "1.5-2.5 nm RTP gate oxides: process feasibility, properties and limitations," Journal of Non-Crystalline Solids, 2001, 280(1-3), p. 32.

Brunette and Chehroudi, "The Effects of the Surface Topography of Micromachined Titanium Substrata on Cell Behavior in Vitro and in Vivo," Journal of Biomechanical Engineering, 121:49 1999.

Brunette, D.M., "Spreading and Orientation of Epithelial Cells on Grooved Substrata," Exp. Cell Res. 167:203, 1986.

Canaud, B, et al., "Mortality risk for patients receiving hemodiafiltration versus hemodialysis: European results from the DOPPS," Kidney Int. 69:2087-2093 (2006).

Chan, CT, et al., "Regression of left ventricular hypertrophy after conversion to nocturnal hemodialysis," Kidney International, 61:2235-9 (2002).

Chung, JH, et al., "Fabrication of nanopores in a 100-nm thick Si3N4 membrane," J Nanosci Nanotechnol. Jul. 2006, vol. 6, No. 7, pp. 2175-2181 (abstract) online. Retrieved on Apr. 18, 2008 from NIH database.

Craighead et al., "Chemical and Topographical Surface Modification for Control of Central Nervous System Cell Adhesion," Biomed. Microdevices, 1:49, 1998.

Curtis and Wilkinson, "Review: Topographical control of cells," Biomaterials 18:24, 1573, 1998.

Davies, "The mesangial cell: A tissue culture view," Kidney International 45:320-327 (1994).

Demetriou et al., "Replacement of Liver Function in Rats by Transplantation of Microcarrier-Attached Hepatocytes," Science 23:233, 1190-1992 1986.

Den Braber et al., "Effect of parallel surface microgrooves and surface energy on cell growth," J. Biomed. Mater. Res. 29:511 1995.

Den Braber et al., "Quantitative analysis of fibroblast morphology on microgrooved surfaces with various groove and ridge dimensions," J. Biomed. Mater. Res. 17:2037, 1996.

Desai, Tejal, "Micro- and nanoscale structures for tissue engineering constructs," Med. Eng. Phys 22:595 2000.

Deutsch et al., "Fabrication of Microtextured Membranes for Cardiac Myocyte Attachment and Orientation," J. Biomed. Mater. Res. 53:267 2000.

Fissell et al., "Ficoll is not a rigid sphere," American Journal of Physiology, Renal Physiology, vol. 293, 2007, p. 1209.

Fissell WH et al., "Initial Characterization of a Nanoengineered Ultrafiltration Membrane," -J. Am Soc Nephrol 2002:13:602A.

Fissell, W.H., et al., "Dialysis and Nanotechnology: Now, 10 Years, or Never?" Blood Purif 2007, 25(1), p. 12.

Guo, L.J., "Recent progress in nanoimprint technology and its applications," Journal of Physics D., Applied Physics, 2004, 37, p. R123.

Heidenhaim AP, et al., "Patient Quality of Life on Quotidian Hemodialysis," AJKD, 42:36-41 (2003).

Humes et al., "Tubulogenesis from isolated single cells of adult mammalian kidney: clonal analysis with a recombinant retrovirus," Amer. J. Physiology, 271:F42, 1996.

Jirka T, et al., "Mortality risk for patients receiving hemodiafiltration versus hemodialysis," Kidney Int 70:1524 (2006).

Kadletz et al., "Implantation of in vitro endothelialized polytetrafluoroethylene grafts in human beings," J. Thoracic and Cardiovascular Surgery 104:736-742, 1992.

Kapur et al., "Fabrication and Selective Surface Modification of 3-Dimensionally Textured Biomedical Polymers from Etched Silicon Substrates," J. Biomed. Mater. Res. 33:205 1996.

Lindsay RM, et al., "Calcium and Phosphate Balance with Quotidian Hemodialysis," American Journal of Kidney Diaseases 42:24-9 (2003).

Lopez, CA, et al., "Evaluation of silicon nanoporous membranes and ECM-based microenvironments on neurosecretory cells," Biomaterials 2006, 27(16), p. 3075.

Mata et al., "Analysis of Connective Tissue Progenitor Cell Behavior on Polydimethylsiloxane Smooth and Channel Micro-Textures," Biomed. Microdevices 4:267, 2002.

Mata et al., "Growth of connective tissue progenitor cells on microtextured polydimethylsiloxane surfaces," J. Biomed. Mater Res. 62:499, 2002.

Mrkisch, et al., "Controlling cell attachment on contoured surfaces with self-assembled monolayers of alkanethiolates on gold," et al. (1996) PNAS 93:10775-10778.

Mrkisch, et al., "Using Microcontact Printing to Pattern the Attachment of Mammalian Cells to Self-Assembled Monolayers of Alkanethiolates on Transparent Films of Godl and Silver," 1997 Exp Cell Research: 305-313.

Mrksich, "A surface chemistry approach to studying cell adhesion," Chem. Soc. Rev. 29:267 (2000).

Nissenson AR, et al., "The Human Nephron Filter: Toward a Continuously Functioning, Implantable Artificial Nephron System," Blood Purification 23(4) 269-74 (2005).

Ohlson M, et al., "Glomerular size and charge selectivity in the rat as revealed by FITC-Ficoll and albumin," Am. J. Physiol Renal Physiol 279:F84-F91 (2000).

Papra A., et al., "Characterization of Ultrathin Poly(ethylene glycol)_Monolayers on Silicon Substrates," Langmuir 17:1457-1460 (2001).

Pierratos A., et al., "Quotidian dialysis—update 2005," Current Opinion in Nephrology & Hypertension 14:119-24 (2005.

Popat and Desai, "Poly(ethylene glycol) interfaces: an approach for enhanced performance of microfluidic systems," Biosensors and Bioelectronics, 2004 19(9).

Rippe, C., et al., "Effects of glomerular filtration rate on Ficoll sieving coefficients (0) in rats," Kidney Int., 2006 69(8) p. 1326.

(56) References Cited

OTHER PUBLICATIONS

Ronco C., et al., "Nanoscale modulation of the pore dimensions, size distribution and structure of a new polysulfone-based high-flux dialysis membrane," IJAO 24:726-735 (2001).

Schneider et al., "Durability of confluent endothelial cell monolayers on small-caliber vascular prostheses in vitro," Surgery 103:456-462 1988.

Scott et al., "The isolation and culture of microvascular endothelium," J. Cell Sci. 105:269-273 1993.

Sharma and Desai, "Nanostructured antifouling oply(ethylene glycol) films for silicon-based microsystems," Journal of Nanoscience and Nanotechnology, 2005 5(2).

Sharma, et al., "Evaluation of the Stability of Nonfouling Ultrathin poly(ethylene glycol) films for silicon-based microdevices," 2004 Langmuir 20(2).

Shepard et al., "Endothelial cell seeding of small-caliber synthetic grafts in the baboon," Surgery 99:318-3 19986.

Shepro et al. "Pericyte physiology," in FASEB J. 7 1031-1038 (1993).

Sims, "Recent advances in pericyte biology-Implications for health and disease," Can. J. Cardiol. 7(10):431-443 (1991).

Stephen RL, et al., "Combined technological-clinical approach to wearable dialysis," Kidney International—Supplement (8):S125-32 Jun. 1978.

Tallal, J., et al., "Replication of sub-40 nm gap nanoelectrodes over an 8-in. substrate by nanoimprint lithography," Microelectronic Engineering, 2005 78-79, p. 676.

Venturoli D and B. Rippe, "Ficoll and dextran vs. globular proteins as probes for testing glomerular permselectivity: effects of molecular size, shape, charge, and deformability," Am. J. Physiol Renal Physiol. 2005 2884(4), p. F605.

Wolfe, et al., "Comparison of Mortality in all patients on dialysis, patients on dialysis awaiting transplantation, and recipients of a first cadaveric transplant," The New England Journal of Medicine, 1999, 341:1725-1730.

Brunette, DM, "Fibroblasts on micromachined substrata orient hierarchically to grooves of different dimensions," Exp Cell Res. 1986;164:11-26.

Chungt, JH, et al., "Fabrication of nanopores in a 100-nm thick Si3N4 membrane," J Nanosci Nanotechnol. Jul. 2006, vol. 6, No. 7, pp. 2175-2181.

Conlisk, AT, et al., "Mass transfer and flow in electrically charged micro- and nanochannels," Anal. Chem. 2002, 74:2139-2150.

Conlisk, AT, et al., "Effect of multivalent ions on electroosmotic flow in micro- and nanochannels," Electrophoresis 24:3006-3017, 2003.

Desai, TA et al., "Nanoporous microsystems for islet cell replacement," Adv. Drug Delivery Rev. 56:1661-1673 (2004).

Desai, TA, et al., "Micromachined interfaces: new approaches in cell immunoisolation and biomulecular separation," Biomolecular Engineering 17 (2000) 23-36.

Park, B., et al., "Micromachining," Med Device Technol. (2002) 13(2): 32-34.

Voldman, J, et al., "Microfabrication in biology and medicine," Annu Rev Biomed Eng (1999) 1: 401-425.

Wagner, B, "Principles of development and design of microsystems," Endosc Surg Allied (1995) 3(4): 204-209.

Whitesides, GM, "Using microcontact printing to pattern the attachment of mammalian cells to self-assembled monolayers of alkanethiolates on transparent films of gold and silver," Exp Cell Research (1997) 235(2):305-313.

Peterson, KE, "Silicon as a Mechanical Material," Proceedings of the IEEE 70(5): 420-457.

Min, et al.,"On the efficiency of electrokinetic pumping of liquids through nanoscale channels," Sensors and Actuators 98:368 (2004).

\* cited by examiner

FIGURE 14
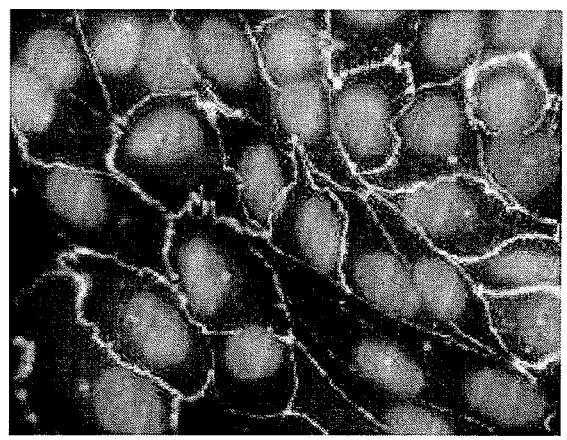
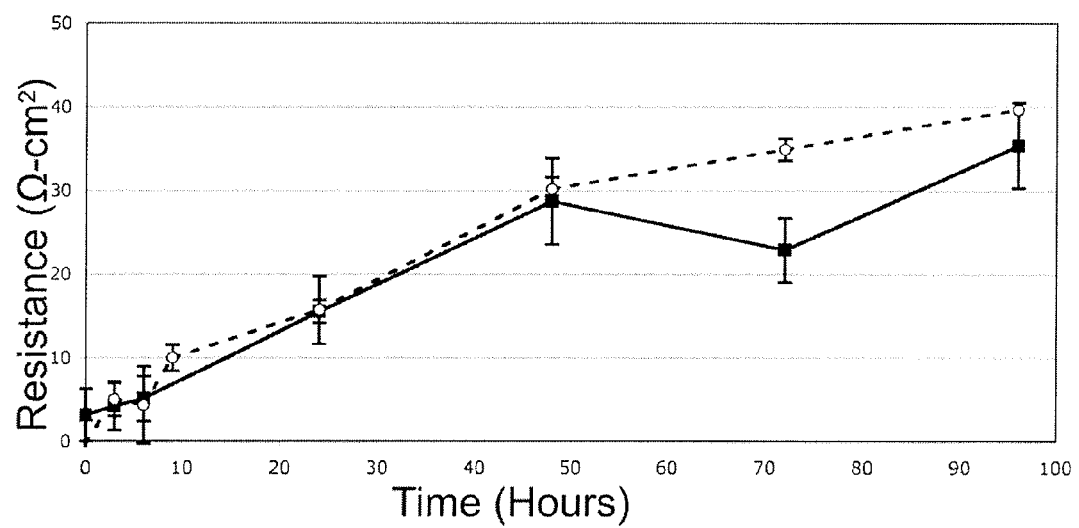

FIGURE 17

(a) The starting material is a SmartCut™ (Soitec USA, Peabody, MA) silicon-on-insulator (SOI) wafer a SOI 500±5 nm-thick SOI layer and a 500 nm-thick buried oxide. First, global alignment keys and polysilicon anchors are etched into the SOI and buried oxide layers using standard photolithography and dry etching techniques. (b) Next, Step and Flash Imprint Lithography (S-FIL) is used to define 50-100 nm slit width and spacing *(see Support letters)*. Alignment is achieved by using the global alignment keys defined in step (a).

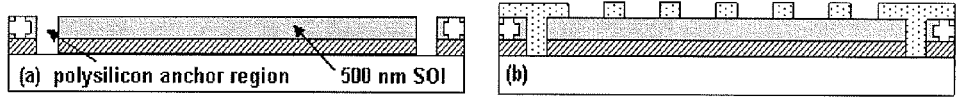

(c) The 500 nm-thick silicon layer is etched using reactive ion etching (RIE). After etching, the S-FIL polymer is removed selectively using a solvent. (d) A 2-10 nm-thick oxide layer is grown on the SOI layer to define the pore size. Photolithography and wet etching is used to form anchors by selectively removing the 2-10 nm-thick oxide so that the subsequent polysilicon layer can bond to the sidewalls of the SOI layer.

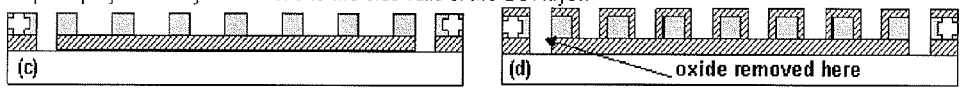

(e) A 750 nm-thick polysilicon layer is deposited and annealed at 1100°C, filling in the gaps between SOI cross bars defined in step (c). (f) Chemical mechanical polishing is used to planarize the front surface. A thin 0.5 µm-thick oxide layer is deposited and removed in the anchor regions.

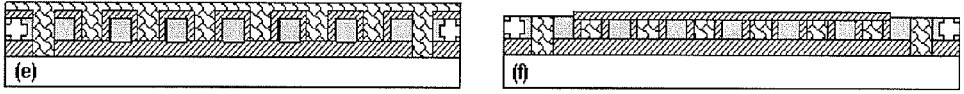

(g) Next, a 4 µm-thick, polysilicon layer is deposited and patterned over the anchors etch in step (d). The oxide in step (f) is an etch-stop layer for patterning of the structural polysilicon layer, which strengthens the membrane many-fold without a reduction in porosity since the polysilicon is only over the anchor regions. Afterwards, 120 nm-thick silicon nitride and 2.0 µm-thick oxide layers are deposited on the wafers. Photolithography and dry etching is used to pattern the oxide and nitride films on the backside of the wafer. Alignment is achieved by using the global alignment targets patterned in step (a). (h) Next, the silicon substrate is etched anisotropically using deep reactive ion etching (DRIE). The buried oxide acts as an etch stop for the DRIE. Lastly, the membrane is released and the nanopores are opened using hydrofluoric acid. The polysilicon moat prevents undercut during the oxide release.

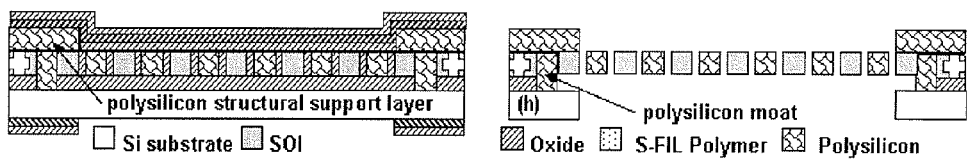

Figure 18

| Membrane Design | #A (no pores) | #B (current) | #C (proposed) |
|---|---|---|---|
| FEM Structure (Quarter Symmetry – Top View) Black lines indicate nanopore sites, while color indicates stress contour (red – highest, blue lowest) Locations for maximum stress are at membrane edges and centers | | | |
| Porosity | 0.0% | 2.2% | 1.2% |
| Fracture Probability | 1.05E-10 | 0.55 | 1.88E-4 |

ULTRAFILTRATION MEMBRANE, DEVICE, BIOARTIFICIAL ORGAN, AND RELATED METHODS

RELATED METHODS

The present application claims priority to U.S. Provisional Patent Application Ser. No. 60/879,744, filed Jan. 10, 2007, which is herein incorporated by reference in its entirety.

This invention was made with government support under DK 50539 awarded by the National Institutes of Health. The government has certain rights in the invention.

FIELD OF THE INVENTION

The present invention relates to ultrafiltration. In particular, the present invention provides nanoporous membranes having pores for generating in vitro and in vivo ultrafiltrate, devices and bioartificial organs utilizing such nanoporous membranes, and related methods (e.g., diagnostic methods, research methods, drug screening). The present invention further provides nanoporous membranes configured to avoid protein fouling.

BACKGROUND OF THE INVENTION

Renal failure affects approximately 300,000 Americans and an unknown number of patients worldwide. Treatment methods of kidney failure currently include organ transplantation and dialysis. Organ transplantation involves a kidney from a cadaver or a living donor implanted in the anterior abdominal wall or the peritoneum of the patient with kidney failure, and the formation of vascular and urinary conduits. Alternatively, two types of dialysis are available: hemodialysis, where the patient's blood is passed against a synthetic or semisynthetic membrane and diffusive transport of toxins occurs into a bath of dialysate on the other side of the membrane, and peritoneal dialysis, wherein the patient's parietal peritoneal epithelium performs the function of the dialysis membrane. Both dialysis methods are performed at scheduled periods of time. All of these treatments are severely limited; organ transplantation is limited by a shortage of donor organs, and dialysis is limited by severe morbidity and mortality. There is evidence that the use of slow continuous ultrafiltration provides benefits when compared with the use of intermittent hemodialysis currently available. There are also components of a bioartificial kidney under development, which may replace some of the endocrine and metabolic functions of the kidney not replaced in hemodialysis.

The replacement of renal function in persons with renal failure by dialysis is dependent on the ability to filter out waste products while preserving metabolically costly proteins, peptides, and cells. In both forms of dialysis, small molecules diffuse from an area of higher concentration (blood) to an area of lower concentration (dialysate), which are separated either by a membrane of cells (the peritoneal lining) in the case of peritoneal dialysis, or a synthetic membrane in the case of hemodialysis. Transport of a molecule from one fluid to the other is proportional to the difference in concentrations of the molecule in the two fluids and is approximately inversely proportional to the molecular size, up to sizes excluded by the membrane. Thus smaller molecules are extracted from the blood more quickly than larger ones. In the native kidney, this is accomplished by a structure called the glomerulus. Blood under arterial pressure enters the glomerular capillary, and water and small solutes are forced through a specialized tissue structure comprised of the cells and connective tissue of the glomerular capillary tuft. The cellular and molecular structure of the glomerulus imposes constraints based on molecular size and molecular charge. Molecules meeting certain size and charge constraints are dragged with the fluid and are transported at a rate directly proportional to the rate of fluid flow. For very small molecules, such as urea, clearance by either method is similar. For very large molecule, such as antibodies, the blockade to passage is similar. For molecules in between, such as β2-microglobulin, convective transport via ultrafiltration may be far more efficient than diffusive clearance through dialysis. β2-microglobulin was selected as an exemplary molecule precisely because it accumulates in renal failure and causes toxicity in the patient, and is not effectively removed by dialysis.

Present hemodialysis requires a bulky hollow-fiber dialyzer that can measure over twelve inches in length and two inches in diameter, and that requires extracorporeal pumps to maintain the blood flow. Such an assembly is not suited to implantation, although wearable external devices have been tested. Furthermore, conventional hemodialysis requires a supply of purified sterile nonpyrogenic water with a balanced electrolyte composition, at flow rates of 400-800 ml/min, which is clearly unsuitable for portable or implantable use. Furthermore, the ideal permselectivity of a dialysis membrane is far from settled, with active research into the relative importance of electrostatic charge versus steric exclusion. Still further, conventional synthetic or semisynthetic membranes have a limited service life due to protein fouling and blood clotting.

What is needed is a filtration membrane which more closely reproduces the filtration functions of the native kidney, both in adopting convective transport of solutes across the membrane and in requiring only modest transmembrane pressures to effect hemofiltration. What is also needed are filtration membranes configured to prevent or decrease protein fouling, resulting in an increased service life.

SUMMARY OF THE INVENTION

The present invention relates to ultrafiltration. In particular, the present invention provides nanoporous membranes having pores for generating in vitro and in vivo ultrafiltrate, devices and bioartificial organs utilizing such nanoporous membranes, and related methods (e.g., diagnostic methods, research methods, drug screening). The present invention further provides nanoporous membranes configured to avoid protein fouling with, for example, a surface coating such as, for example, polyethylene glycol, oligosaccharide surfactant polymers, heparin, and hyaluronan. The present invention is not limited to a particular type of membrane material. In some embodiments, the material of the membrane is, for example, silicon, polysilicon, silicon carbide, ultrananocrystalline diamond, diamond-like-carbond (DLC), silicon dioxide, PMMA, SU-8, PTFE, titanium, silica, silicon nitride, polytetrafluoroethylene, polymethylmethacrylate, polystyrene, and/or silicone. In some embodiments, the membranes are associated with sensors configured to monitor, for example, filtration parameters. Examples of such sensors include, but are not limited to, pressure sensors configured to monitor transmembrane pressure, protein sensors configured to monitor protein leakage/membrane breakdown, optical blood sensors configured to monitor membrane rupture, and urea sensors configured to monitor urea clearance.

It is not obvious to those skilled in the art that a protein-free ultrafiltrate generated by the devices of the present invention may be in itself valuable and useful for ends other than the removal of toxins in blood filtering applications. For example, the ultrafiltration devices of the present invention also find use in diagnostic applications. For example, the devices provides a means for selectively screening out undesired molecules (e.g., proteins) within fluids, such that a particular analyte to be analyzed (e.g., small molecules such as glucose, lactic acid, electrolytes, ions, including, but not limited to, potassium, sodium, calcium, chloride, oxygen, and carbon dioxide) in the absence of interfering molecules. Present electrochemical sensors for glucose measurement are severely hampered by protein fouling of the sensor, and great effort is devoted to the invention of fouling retardants to prolong sensor life. An ultrafiltrate substantially free of proteins, but still containing smaller constituents of blood, including but not limited to sodium, potassium, chloride, glucose, provides a solution to assay for glucose concentration without protein fouling. Thus, the present invention further provides systems for use in the analysis of small molecule, including, but not limited to those listed above. Furthermore, as the intracellular aqueous milieu differs from extracellular fluid, the separate testing of whole blood and a protein and cell-free ultrafiltrate for electrolyte compositions, magnetic susceptance, optical, infrared, or magnetic resonance spectroscopy, and other physical properties of matter, provides detailed information regarding the cellular composition of the blood.

Furthermore, it is not obvious to those skilled in the art that a protein and cell free ultrafiltrate of blood so generated may be in itself valuable and useful for ends other than the removal of toxins and the measurement of the constituents of blood. The constituents of blood necessary for at least temporary support of a metabolically active cell are small in molecular size (including but not limited to oxygen, glucose, insulin, triiodothyronine, and retinoic acid, for example) while those immune mediators responsible for rejection of an allograft or xenograft are large in molecular size, such as antibodies, or components of the complement cascade, or reside in cell membranes, such as the major histocompatibility complexes. Thus a stream of ultrafiltrate of blood may be used to supply nutrients and carry away wastes by an efficient convective transport process, rather than by less efficient diffusive transport. This is directly applicable to any generalized cell population considered for transplantation, including but not limited to islet cell transplantation, liver cell transplantation, kidney cell transplantation, and in general transplant of any allo- or xeno-geneic cell type.

The ultrafiltration devices of the present invention also provide bioreactors for the growth of cells or tissues. In some such embodiments, the cells or tissues are grown with a chamber of the device such that the media in which the cells or tissues is bathed is selectively screened by the membranes of the device.

The present invention also provides bioartificial organs for in vivo or extracorporeal uses. In some embodiments, the bioartificial organs comprise cells attached to or associated with a surface. In some such embodiments, the surface is modified to control the biological activity of the attached or associated cells. In some preferred embodiments, the surface is a membrane of the present invention, having pores, as described herein. However, the present invention is not limited to the use of surfaces that comprise the membranes of the present invention.

In some embodiments, the present invention provides systems, methods and devices that utilize a defined pore shape and structure which may incorporate electrodes or other devices, chemicals, and treatments within or around a pore structure to control charge and/or size selectivity of the pore.

The present invention also provides systems and methods of using such pores to produce an ultrafiltrate; in particular, such methods are used to produce an ultrafiltrate of plasma, thereby accomplishing hemofiltration and/or hemodialysis.

For example, in some embodiments, the present invention provides a membrane comprising nanofabricated pores, where each pore comprises a pore structure of defined dimensions and structure, and density. In further embodiments, at least one pore of the membrane and/or optionally at least a portion of the membrane surface comprises at least one surface treatment. Surface treatments include but are not limited to treatments that limit protein adsorption, treatments that alter or confer surface charge and surface free energy and treatments that promote adhesion of specific cell types. In other embodiments, at least one pore of the membrane comprises at least one electrode positioned on or near the membrane and/or pore such that an electric field is generated in or near the nanofabricated pore. In yet other embodiments, at least one pore of the membrane comprises any combination of a surface treatment, or any combination of a surface treatment and at least one electrode. Surface treatments and/or electric fields function to effect restriction of size and electrostatic charge of solutes that may be passed through such pores.

In other embodiments, the present invention provides an ultrafiltration system comprising: 1) a membrane comprising nanofabricated pores as described above; 2) an electrode or other device, technique, or modification to generate an electric field positioned on or near the membrane and/or pore such that an electric field is generated in or near the nanofabricated pores; 3) a housing containing the membrane and the electrode; and a fluid delivery passageway with a first end and a second end, said first end positioned outside of the housing, the second end positioned to deliver fluid across the membrane. In further embodiments, the system further comprises a membrane comprising nanofabricated pores as described, wherein the membrane also comprises a surface treatment of at least one pore and/or of the membrane, wherein the surface treatment functions to promote or retard attachment of specific cells and proteins.

In preferred embodiments, the system is configured to receive and deliver blood or plasma directly or indirectly from a subject's vasculature. In some embodiments, the housing is very small, allowing the system to be maintained on or in a subject. For example, in some preferred embodiments, the housing is made of or coated in a biocompatible material and is implanted into a subject to provide continuous hemofiltration and/or hemodialysis. In some embodiments, the system is attached to one or more additional devices that process, store, or otherwise manipulate a biological fluid and/or collect and analyze data.

In some embodiments, the system further comprises a pump configured to pass fluid through the fluid delivery passageway. In yet other embodiments, the system further comprises an actuator (e.g., a nanoscale actuator) that decreases protein fouling of the pores during fluid processing.

The present invention also provides methods of filtering a biological fluid. For example, in some embodiments, the present invention provides a method having the steps of, 1) providing a biological fluid (e.g., from a subject) and an ultrafiltration system (e.g., as described above, or elsewhere herein); 2) transferring the biological fluid into the ultrafiltration system (e.g., into the first end of the fluid passageway); 3) passing the fluid across a membrane to generated filtered fluid; and, in some embodiments, 4) transferring the filtered fluid to a subject. In some preferred embodiments, the filtered fluid that is generated is substantially free of proteins. Thus, in some embodiments, the method produces hemofiltered and/or hemodialyzed fluid.

In some preferred methods, an electric field is provided in or around at least one nanofabricated pore in the membrane. In some embodiments, the electric field is produced under conditions such that the pores provide a charge and/or size selective barrier to proteins. In some embodiments, the electric field is produced under conditions such that protein fouling is reduced in the pores.

In some embodiments, the present invention provides an ultrafiltration system comprising: a) a membrane comprising micromachined pores having a length and a width, said length being less than 500 microns (e.g., less than 200, less than 100, less than 50, less than 20, less than 10, etc. microns) and said width being less than 500 nanometers (e.g., less than 200, less than 100, less than 50, less than 20, less than 10, . . . nanometers), wherein the ratio of said length to said width is at least 2:1 (e.g., 3:1, 4:1, 5:1, 8:1, 10:1, . . . etc.); a housing containing said membrane; and a fluid delivery passageway with a first end and a second end, said first end positioned outside of said housing, said second end positioned to delivery fluid across said membrane. In preferred embodiments, the housing comprises a biocompatible coating that permits the system to be used in vivo. In some embodiments, the system further comprises one or more electrodes positioned on or near said membrane such that an electric field is generated in or near said pores. In some embodiments, the housing has a length and a width, said length of said housing being less than 500 millimeters (e.g., less than 400, 300, 200, 100, . . . ) and said width of said housing being less than 500 millimeters (e.g., less than 400, 300, 200, 100, . . . ).

The present invention further provides an ultrafiltration system comprising a membrane comprising a plurality of micromachined pores, wherein the length (the longest dimension) of each of said plurality of micromachined pores differs from the length from the other micromachined pores by no more than 30% (e.g., 20%, 10%, 5%, . . . ). In some embodiments, the width (the shortest dimension) of each of the plurality of micromachined pores differs from the shortest dimension of the other micromachined pores by no more than 30% (e.g., 20%, 10%, 5%, . . . ).

The present invention further provides an ultrafiltration system comprising a plurality of membranes, wherein each of the membranes comprises a plurality of micromachined pores, wherein the shortest dimension of each of the plurality of micromachined pores differs from the shortest dimension of the other micromachined pores by not more than 30% (e.g., 20%, 10%, 5%, . . . ).

The present invention also provides an implantable ultrafiltration device comprising: a membrane comprising micromachined pores configured to permit ultrafiltration of blood under systolic blood pressure (e.g., without the use of a pump); a biocompatible housing containing said membrane; and a fluid delivery passageway with a first end and a second end, said first end positioned outside of said housing, said second end positioned to delivery fluid across said membrane.

The present invention further provides a diagnostic ultrafiltration device comprising a any of the above membranes; a housing containing said membrane; a fluid delivery passageway with a first end and a second end, said first end positioned outside of said housing, said second end positioned to delivery fluid across said membrane and into a chamber enclosed by said housing; and a sensor contained in said chamber, said sensor configure to detect an analyte (e.g., glucose, a pathogen, a portion of a pathogen, etc.).

The present invention also provides a bioartificial ultrafiltration device, comprising: a housing; an inlet port passing through said housing, said inlet port configured to receive a biological fluid; an outlet port passing through said housing, said outlet port configured to return a biological fluid to a subject; a membrane contained in said housing, said membrane comprising micromachined pores (e.g., any membrane disclosed herein); and a population of cells attached to said membrane. In preferred embodiments, the housing is of a size and is made of a biocompatible material to allow in vivo use. In some embodiments, the device further comprises one or more electrodes positioned on or near said membrane such that an electric field is generated in or near said pores. In some embodiments, the population of cells comprises renal proximal tubule cells. In some embodiments, a membrane prevents passage of cells or components of cells, as well as subcellular components, into said outlet port or into particular chambers of the device.

The present invention further provides a bioartificial ultrafiltration device, comprising: a housing; an inlet port passing through said housing, said inlet port configured to receive a biological fluid, an outlet port passing through said housing, said outlet port configured to return a biological fluid to a subject, a textured surface contained in said housing, said textured surface configured to support the attachment, growth, normal biological function (e.g., normal protein expression), or differentiation of kidney tissue; and a population of cells attached to said membrane. In some embodiments, the textured surface comprises a silicon surface (e.g., silicon or polysilicon). In some preferred embodiments, the silicon surface comprises a single-crystal silicon surface. In some embodiments, the surface is coated with extracellular matrix proteins. In some embodiments, the cells comprise renal tubule cells, pancreatic cells, hepatic cells, thyroid cells, adrenal cells, parathyroid cells, pituitary cells, hypothalamic cells, gonadal cells, prokaryotic cells, duodenal cells, other intestinal cells, gastric cells, muscle cells, fibroblast cells, and endothelial cells. In preferred embodiments, the surface is configured such that the renal tubule cells express tight junction proteins. In some preferred embodiments, the surface is prepared by generating an oxide layer, followed by deposition of a polysilicon film.

In some embodiments, the membranes of the present invention do not require blood pumps to operate, and as such, simplifies wearable and/or implantable dialysis. In some embodiments, the present invention provides membranes for ultrafiltration with well-defined, slit-shaped pores. In some embodiments, the membranes are designed and assembled using silicon bulk and surface micromachining techniques. In some embodiments, the membranes are further surface modified with poly (ethylene glycol) (PEG). Experiment conducted during the development of the present invention demonstrated that hydraulic permeability of such membranes was stable despite perfusion with albumin, showing that membrane fouling by BSA, or the Ficoll polymer, did not occur. Conventional polymer dialyzers are estimated to have a mean pore diameter around 30 angstrom units (Å), with pore size distributions encompassing a range possibly double that (see, e.g., Ronco C, et al., IJAO 24:726-735 (2001); incorporated herein by reference in its entirety). Hydraulic permeability calculations for the silicon membrane provided by particular examples of the present invention estimate a pore size of 67 Å by 45 microns. Despite a mean pore size more than twice that of the polymer membrane in these specific examples, more stringent size exclusion was observed. A doubling in mean pore size showed a fourfold improvement in specific hydraulic permeability (hydraulic permeability normalized to membrane porosity).

In certain embodiments, the present invention provides membranes comprising a plurality of nanofabricated pores. The present invention is not limited to a particular type, kind or size of membrane comprising a plurality of nanofabricated pores. In some embodiments, the membrane has a surface coating of polyethylene glycol. In some embodiments, the plurality of nanofabricated pores have a width less than 100 nanometer (e.g., less than 50, less than 20 nanometers, etc.). In some embodiments, the distance (e.g., average distance) between each of the plurality of nanofabricated pores is less than 500 nanometers (e.g., less than 50 nanometers, 100 nanometers, 150 nanometers, 200 nanometers). In some embodiments, the length of the nanofabricated pores is less than 200 μm (e.g., less than 100 μm, 50 μm, 40 μm, 30 μm, 10 μm). In some embodiments, the plurality of nanofabricated pores have a slit shape.

In certain embodiments, the present invention provides an ultrafiltration system comprising a) a membrane comprising a plurality of nanofabricated pores; b) a housing containing the membrane; and c) a fluid delivery passageway with a first end and a second end, the first end positioned outside of the housing, the second end positioned to delivery fluid across the membrane.

In some embodiments, the housing comprises a coating, the coating being biocompatible for in vivo use. In some embodiments, the housing is configured for implantation into an animal (e.g., a human). In some embodiments, the housing has a length and a width, the length of the housing being less than 300 millimeters (e.g., 300 millimeters, 250 millimeters, 200 millimeters, 175 millimeters, 100 millimeters) and the width of the housing being less than 300 millimeters (e.g., 300 millimeters, 250 millimeters, 200 millimeters, 175 millimeters, 100 millimeters).

In some embodiments, the system further comprises one or more electrodes positioned on or near the membrane such that an electric field is generated in or near the pores.

In some embodiments, the system further comprises one or more electrodes positioned on or near the membrane such that an electric field is generated in or near the pores.

In certain embodiments, the present invention provides methods of filtering a biological fluid comprising a) providing i) a biological fluid; and ii) an ultrafiltration system comprising a) a membrane comprising a plurality of nanofabricated pores having a width less than 100 nanometers (e.g., less than 20 nanometers); the membrane optionally having a surface coating of polyethylene glycol; b) a housing containing the membrane; and c) a fluid delivery passageway with a first end and a second end, the first end positioned outside of the housing, the second end positioned to deliver fluid across the membrane; and b) transferring the biological fluid into the first end of the delivery passageway; and c) passing the fluid across the membrane to generated filtered fluid. In some embodiments, the method further comprises the step of d) transferring the filtered fluid into a subject. In some embodiments, the filtered fluid is substantially free of proteins. In some embodiments, the filtered fluid comprises hemofiltered fluid.

In certain embodiments, the present invention provides an implantable ultrafiltration device comprising a) a membrane comprising a plurality of nanofabricated pores having a width less than 100 nanometers (e.g., less than 20 nanometers); the membrane optionally having a surface coating of polyethylene glycol; b) a biocompatible housing containing the membrane; and c) a fluid delivery passageway with a first end and a second end, the first end positioned outside of the housing, the second end positioned to delivery fluid across the membrane. In some embodiments, the housing comprises a coating, the coating being biocompatible for in vivo use. In some embodiments, the device further comprises a population of cells attached to the membrane. In some embodiments, the cells are selected from the group consisting of renal tubule cells, pancreatic cells, hepatic cells, thyroid cells, adrenal cells, parathyroid cells, pituitary cells, hypothalamic cells, gonadal cells, prokaryotic cells, duodenal cells, gastric cells, intestinal cells, muscle cells, fibroblast cells, and endothelial cells. In some embodiments, the housing has physical dimensions that permit the device to be used in a human subject, in vivo.

In certain embodiments, the present invention provides methods for creating an implantable ultrafiltration device comprising imprinting a plurality of nanofabricated pores having a width of less than 20 nanometers onto the surface of a membrane, wherein said nanofabricated pores are positioned in the center of said membrane surface. In some embodiments, the imprinting is accomplished with nanolithography. In some embodiments, the membrane has a surface coating selected from the group consisting of polyethylene glycol, oligosaccharide surfactant polymers, heparin, and hyaluronan. In some embodiments, the membrane has a porosity below 2%.

BRIEF DESCRIPTION OF THE DRAWINGS

FIG. 14 Left shows human renal tubule epithelial cell growth on silicon nanoporous membranes. Renal tubular epithelial cells stained for a tight junction protein, ZO-1 (green), a ciliary protein, acetylated tubulin (red), a brush border enzyme, γ-glutamyl transferase (not shown), and a nuclear stain (blue). FIG. 14 RIGHT shows transepithelial resistance of renal tubule epithelial cells on silicon nanoporous membranes is comparable to conventional polyester controls (dashed line) for 0-96 hours in culture.

FIG. 17 shows fabrication of silicon nanoporous membranes using MEMS and nanoimprint lithography technology. Cross-sectional schematics depict the wafer at various stages of fabrication. These drawings are not drawn to scale in order to show the details of the cross-sectional flow.

FIG. 18 shows the stress fields and fracture probability of three membrane designs. Design #A shows a baseline solid membrane without any pores, while Design #B presents a membrane design having 2.9% porosity wherein the pores are distributed all over the membrane including the edge and center regions. The corresponding fracture probabilities (~0% for Design #A and 55% for Design #B) indicate that current membrane designs are fragile and fracture slightly above 3 psi, while the solid membranes survive 100 psi transmembrane pressures. In contrast, pore distribution in Design #C has been optimized to avoid membrane edges and the center region, which results in a very low fracture probability (~0%).

DEFINITIONS

Figure 1:
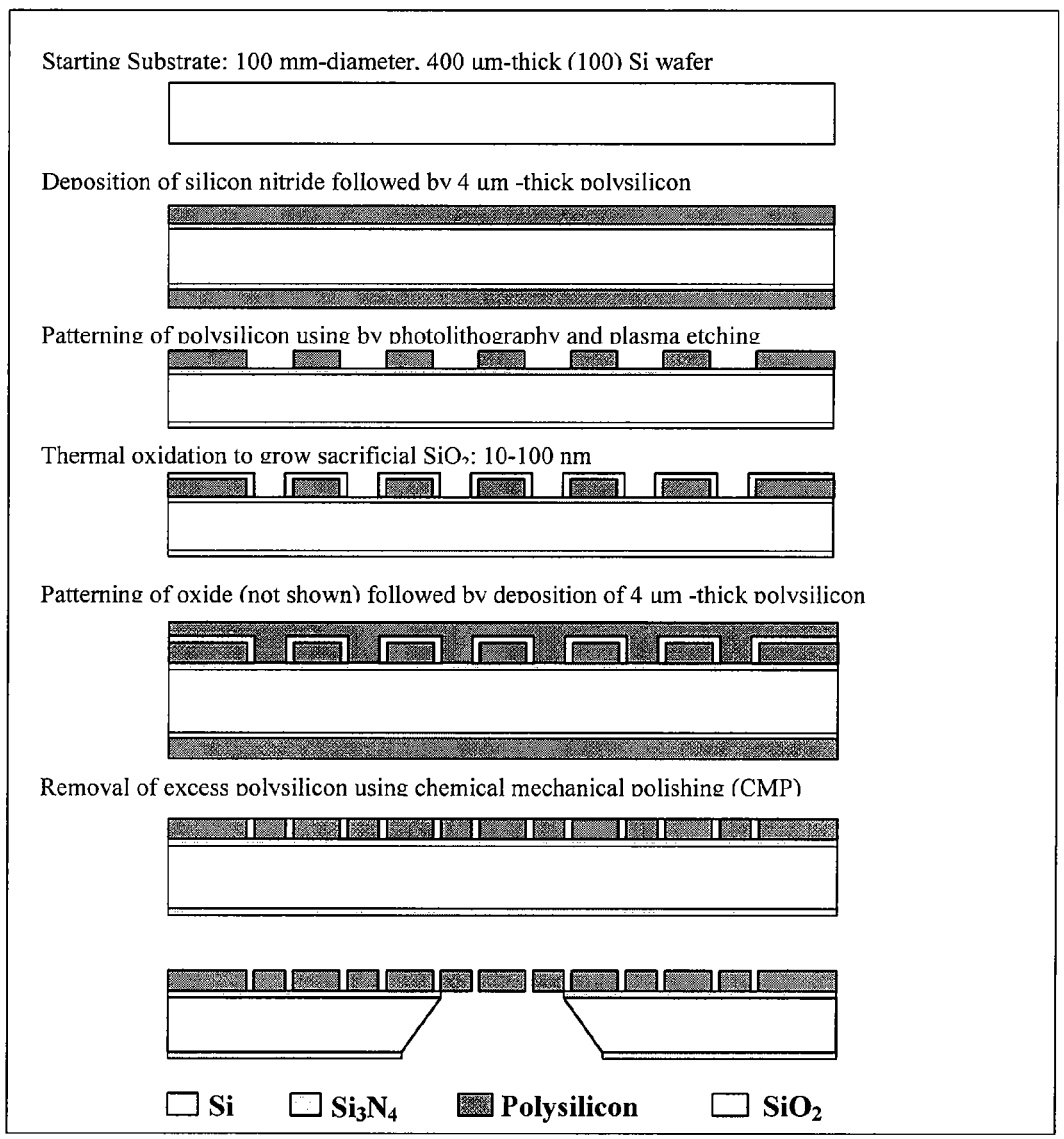
FIG. 1 shows a schematic description of process flow for the fabrication of nanoporous membranes showing wafer cross-sections.

To facilitate an understanding of the present invention, a number of terms and phrases as used herein are defined below:

As used herein, the term "filtration" refers to a process of separating particulate matter from a fluid, such as air or a liquid, by passing the fluid carrier through a medium that will not pass the particulates.

As used herein, the term "ultrafiltration" refers to subjecting a fluid to filtration, where the filtered material is very small; typically, the fluid comprises colloidal, dissolved solutes or very fine solid materials, and the filter is a microporous, nanoporous, or semi-permeable medium. A typical medium is a membrane. The fluid to be filtered is referred to as the "feed fluid." During ultrafiltration, the feed fluid is separated into a "permeate" or "filtrate" or "ultrafiltrate," which has been filtered through the medium, and a "retentate," which is that part of the feed fluid which did not get filtered through the medium, or which is retained by the medium.

As used herein, the term "dialysis" refers to a form of filtration, or a process of selective diffusion through a membrane; it is typically used to separate low-molecular weight solutes that diffuse through the membrane from the colloidal and high-molecular weight solutes which do not. In some embodiments, a feed of fluid is passed over a semipermeable membrane, and a feed of dialysate is passed over the other side of that membrane; the membrane is wetted by one or both solvents, and then there is diffusive transport of dissolved solutes between the fluids. The composition of one fluid, the dialysate, is used to deplete the composition of the other fluid, the feed fluid, of some molecule or molecules.

As used herein, the term "dialysate" is used to refer to the fluid into which low-molecular weight solutes diffuse through a membrane from another fluid (typically, the feed fluid) initially containing these solutes.

As used herein, the term "free of" refers to fluids of mixtures that have had one or more components (e.g., protein components) removed. "Substantially free of" fluids or mixtures are at least 50% free, preferably at least 75% free, and more preferably at least 90% free from a component with which they are otherwise naturally associated. For example, a fluid that is "substantially free of protein" is a fluid that has at least 50% or less of the protein content of an unfiltered or unpurified fluid.

As used herein, the term "microelectronics" refers to a branch of electronics that deals with the miniaturization of electronic components.

As used herein, the term "microchip" refers to another term for microsized electronic components using integrated circuit technology.

As used herein, the term "microelectromechanical systems" refers to devices that involve integrated microdevices or systems, combined with electrical and mechanical components, produced using microelectronics-compatible batch-processing techniques. These systems merge computation with sensing and actuation to perceive the physical world at a miniaturized level.

As used herein, the term "MEMS" refers to a mnemonic for microelectromechanical systems.

As used herein, the term "microfluidics" refers to MEMS devices used for the movement of fluids or gases to create microscale chemical analysis systems. This technology is becoming widely used in ink-jet printing devices for increased accuracy and resolution. It is also being investigated for its use in DNA analysis and synthesis where minute quantities of fluid are needed to assess the biochemical makeup of a cell or protein.

As used herein, the term "microfabrication" refers to a processing techniques used to manufacture microelectronics components. Typical techniques are deposition, photolithography, etching, and doping.

As used herein, the term "micromachining" refers to mechanical and chemical fabrication processes that were used to form these micromechanical parts, such as by etching areas of the silicon substrate away to leave behind the desired geometries. The development of silicon microsensors often required the fabrication of micromechanical parts (e.g., a diaphragm in the case of the pressure sensor and a suspension beam for many accelerometers). These micromechanical parts were fabricated by selectively etching areas of the silicon substrate away to leave behind the desired geometries. Hence, the term micromachining came into use in the early 1980s. Micromachining designates the mechanical fabrication processes that were used to form these micromechanical parts. The successful incorporation of techniques for the selective etching of silicon (which were initially investigated in the 1960's and 1970's), with advances in microfabrication, provided the process flexibility that was necessary to fashion micromechanical parts from silicon and related microelectronics fabrication materials.

As used herein, the term "polysilicon" refers to a polycrystalline form of silicon that is deposited as a thin film. It is used in microelectronics for transistors and wiring. In MEMS, polysilicon is usually used as structural material for devices.

As used herein the term "animal" refers to any member of the kingdom Animalia that includes living things which have cells differing from plant cells with regard to the absence of a cell wall and chlorophyll and the capacity for spontaneous movement. Preferred embodiments of the present invention are primarily directed to vertebrate (backbone or notochord) members of the animal kingdom.

As used herein, the term "subject" refers to any animal (e.g., a mammal), including, but not limited to, humans, non-human primates, rodents, and the like, which is to be the recipient of a particular diagnostic test or treatment. Typically, the terms "subject" and "patient" are used interchangeably herein in reference to a human subject.

The terms "sample" and "specimen" in the present specification and claims are used in their broadest sense. On the one hand, they are meant to include a specimen or culture. On the other hand, they are meant to include both biological and environmental samples. These terms encompasses all types of samples obtained from humans and other animals and plants, including but not limited to, body fluids such as urine, blood, fecal matter, cerebrospinal fluid (CSF), semen, and saliva, as well as solid tissue, sap, and nectar. However, these examples are not to be construed as limiting the sample types applicable to the present invention.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

DETAILED DESCRIPTION

The kidney is unique in that it is the first organ for which long-term ex vivo substitutive therapy has been available and lifesaving. Renal failure prior to the era of hemodialysis and transplantation resulted in certain death, and this outcome of renal failure is still current outside the industrialized world.

In the United States, 452,000 patients were listed as having end-stage renal disease (ESRD) by the 2005 USRDS database, of whom 324,826 were receiving maintenance dialysis (see, e.g., U.S. Renal Data System, USRDS 2005 Annual Data Report: Atlas of End-Stage Renal Disease in the United States, National Institutes of Health, National Institute of Diabetes and Digestive and Kidney Diseases, Bethesda, Md. 20002; incorporated herein by reference in its entirety). The prevalence of ESRD in the United States is rising at approximately 8% per year (see, e.g., U.S. Renal Data System, USRDS 2005 Annual Data Report: Atlas of End-Stage Renal Disease in the United States, National Institutes of Health, National Institute of Diabetes and Digestive and Kidney Diseases, Bethesda, Md. 20002; Neilson E G et al: The Ad Hoc Committee Report on estimating the future workforce and training requirements for nephrology. JASN 1997; 8:S1-S4; each incorporated herein by reference in their entireties). The financial cost of dialysis is immense, estimated at 64,614 USD per hemodialysis patient per year and 47,384 USD per peritoneal dialysis patient per year. In contrast, transplant patients cost an average of 22,142 USD per patient per year (see, e.g., U.S. Renal Data System, USRDS 2005 Annual Data Report: Atlas of End-Stage Renal Disease in the United States, National Institutes of Health, National Institute of Diabetes and Digestive and Kidney Diseases, Bethesda, Md. 20002; incorporated herein by reference in its entirety).

The higher cost of maintenance dialysis when compared with transplantation does not translate into better results; annual mortality for patients listed for transplant and awaiting a kidney is 6.3%, compared with only 3.8% for patients listed for transplant who did receive a kidney. These statistics compare favorably to the 16.7% annual mortality for ESRD patients not listed for transplant (see, e.g., Wolfe R A et al: Comparison of mortality in all patients on dialysis, patients on dialysis awaiting transplantation, and recipients of a first cadaveric transplant. NEJM 1999; 341:1725-1730; incorporated herein by reference in its entirety). Transplantation, despite its advantages in terms of cost, morbidity, and mortality, is severely limited by scarcity of donor organs. In 2006, there are over 300,000 patients on dialysis and 72,983 patients on the kidney wait list. Only 4096 renal transplants were performed in the first quarter of 2006, based on Organ Procurement and Transplantation.

Frequent prolonged dialysis administered at home reduces comorbidities and enhances patient lifestyle at significantly reduced cost, but the labor, risk, and inconvenience of conventional dialysis may limit acceptance outside of a clinical trial environment (see, e.g., Pierratos A., et al, Quotidian dialysis—update 2005 Current Opinion in Nephrology & Hypertension. 14:119-24 (2005); Chan C T, et al., Kidney International. 61:2235-9 (2002); Lindsay R M, et al., American Journal of Kidney Diseases. 42:24-9 (2003); Heidenheim A P; et al., AJKD. 42:36-41 (2003); each incorporated herein by reference in their entireties). Recent data suggest that convective or mixed convective-diffusive therapies are associated with enhanced survival compared with diffusive therapies alone (see, e.g., Canaud B, et al., Kidney Int. 69:2087-2093 (2006); Jirka T, et al., Kidney Int 70:1524 (2006); each incorporated herein by reference in their entireties).

Prolonged hemodiafiltration or hemofiltration at home improves outcomes in ESRD care. However, technology is not in place to facilitate widespread adoption of a home hemofiltration program. Hemodialysis and hemofiltration cartridges in present clinical use require superphysiologic pressures for blood flow through hollow fiber membranes and to drive ultrafiltration. These pressures necessitate roller pumps and a cumbersome extracorporeal circuit, as well as percutaneous vascular access. Achievement of clinically significant ultrafiltration rates with physiologic pressures (20-50 mmHg) will simplify engineering of a wearable or implantable dialysis cartridge. The advantages of an implanted dialysis system include, for example, portability, the safety inherent in elimination of the extracorporeal blood circuit, as well as the relocation of the transcutaneous access to the dialysate side of the circuit, possibly further reducing infection and bleeding.

For convective therapies, an estimate of the hydraulic permeability needed to provide adequate small-solute clearance can be obtained by dividing a minimum ultrafiltration rate, e.g. 30 ml/min, by capillary perfusion pressure, e.g., 30 mm Hg, obtaining a rough estimate of 1 ml/min/mmHg. Conventional polymer dialysis membranes have ultrafiltration coefficients ($K_{UF}$) of approximately 11-85 ml/hour/mmHg (0.18-1.41 ml/min/mmHg), in packages providing 1-2 m² membrane area (see, e.g., Canaud B, et al., Kidney Int. 69:2087-2093 (2006); incorporated herein by reference in its entirety). These hydraulic data do not incorporate the additional pressure head needed to move blood along the length of the hollow fiber. These pressures, as well as the package size of the dialyzer, dictate that present systems are limited to extracorporeal use.

Maximizing hydraulic permeability, or, reciprocally, minimizing membrane area, is a function of membrane pore geometry. Ronco et al have reviewed the relationship between pore dimension, size dispersion, and $K_{UF}$ (see, e.g., Ronco C, et al., IJAO 24:726-735 (2001); incorporated herein by reference in its entirety). In particular, the importance of a narrow pore size distribution in maximizing hydraulic permeability while limiting albumin leakage is identified. In addition to pore size distribution, membrane thickness and pore shape also influence hydraulic permeability. Nature has repeatedly evolved slit-shaped or plate-shaped structures where pressure-driven filtration occurs, such as in the podocyte slit diaphragm, the bills of filter feeding birds such as shovelers and flamingoes, and in the baleen plates of filter feeding whales. Elongated, slit-shaped pores are predicted to have high hydraulic permeability per area of membrane, up to a theoretic maximum of about a 2.6-fold increase over round pores.

The present invention provides a compact ultrafiltration device and methods for generating an ultrafiltrate, both of which can be used for a variety of applications, including, but not limited to filtering blood, diagnostic applications, as a bioreactor, in bioartificial organs, etc. The present invention also provides a nano-machined porous structure that permits individual control of pore size and charge density.

For example, in some embodiments, the present invention provides a membrane comprising a plurality of pores, where the shapes and sizes of the pores are highly controlled. In some embodiments, the membrane further comprises at least one surface treatment. In other embodiments, the membrane further comprises at least one electric field generator, such that an electric field is produced in or around at least one pore; examples of electric field generators include but are not limited to electrodes. In yet other embodiments, the membrane further comprises at least one surface treatment and at least one electric field generator, such that an electric field is produced in or around at least one pore; examples of electric field generators include but are not limited to electrodes. In yet further embodiments, the membrane further comprises at least one of a pump and an actuator; in yet further embodiments, the membrane further comprises at least one of a surface treatment, an electric field generator, such that an electric field is produced in or around at least one pore, a pump, and an actuator.

The present invention also provides a system comprising a compartment and the porous membrane of the present invention as described above, where the porous membrane is supported within the compartment of the device, such that the presence of the membrane separates the compartment into two sub-compartments. A housing defines the outer surfaces of the compartments. A housing may be composed of any desired material. Where the system is used on or in a subject, the housing is preferably made of or coated with a biocompatible material.

Unlike the system of the prior art, the present invention provides a system that permits complete manipulation of parameters to control exclusion of molecules with particular properties (e.g., size, molecular charge, etc.). The prior art systems also do not permit exclusion of molecules within tight property parameters (e.g., sharp size, molecular charge, etc. cut-offs). Furthermore, the prior art systems do not provide ultrafiltration systems that can be used in vivo under biological pressures. Such systems would require the use of pumps to function under biological pressures, pumps that are too large for practical in vivo use.

Wearable or implantable dialysis has been repeatedly proposed since dialysis was first implemented as treatment for end-stage renal disease (see, e.g., Ohlson M, et al., Am. J. Physiol Renal Physiol 279:F84-F91 (2000); Stephen R L., et al., Kidney International—Supplement. (8):S125-32, 1978 June; Nissenson A R, et al., Blood Purification. 23(4):269-74, 2005; each herein incorporated in their entireties). Miniaturizing the extracorporeal circuit has been challenging in design of pumps that can circulate blood through hollow fiber dialyzers (see, e.g., Nissenson A R, et al., Blood Purification. 23(4):269-74, 2005; herein incorporated by reference in its entirety). In some embodiments of the present invention, the membranes do not require blood pumps to operate, and as such, simplifies wearable and/or implantable dialysis. Accordingly, the present invention relates to ultrafiltration. In particular, the present invention provides nanoporous membranes having slit pores for generating in vitro and in vivo ultrafiltrate, devices and bioartificial organs utilizing such nanoporous membranes, and related methods (e.g., diagnostic methods, empirical methods, drug screening). The present invention further provides nanoporous membranes configured to avoid protein fouling with, for example, a polyethylene glycol surface coating.

I. Membranes

Existing polymer membranes used in dialysis and ultrafiltration are unsuitable for use in implantable bioartificial kidneys, as they have low hydraulic permeability and result in prohibitively large package size. These membranes are typically produced by formed by extrusion and solvent casting techniques. The geometry and surface chemistry of the pores arise from the chemistry of the polymers and the fluid dynamics of the casting process. In general, the hollow-fiber membranes are fairly thick or employ a multilayer scaffold for mechanical support, and have a distribution of pore sizes rather than a regular array of uniform pores. Pores in conventional polymeric membranes tend to be either roughly cylindrical, have a round orifice terminating a larger channel, or have a structure resembling an open-cell sponge.

The wide dispersion in pore sizes within a membrane leads to imperfect retention of molecules larger than the mean pore size of the membrane. This effect is remedied in practice by engineering the mean pore size of the membrane to be sufficiently small that negligibly few pores are so large as to allow passage of a solute above the desired molecular weight cutoff of the membrane. Unfortunately, this approach has the undesired effect of reducing the mean pore size in the membrane and thus reducing the hydraulic permeability of the membrane. The membranes of the present invention overcome these problems with narrower pore size distributions, allowing sharper transitions from passage to retention and maximizing the mean pore size of the membrane (e.g., nanoporous membranes having slit pores).

In some embodiments, the present invention provides membranes configured for filtration of biological fluids (e.g., dialysis). The present invention is not limited to a particular type of membrane. In some embodiments, the membrane comprises a plurality of pores, where the shapes and sizes of the pores are highly controlled. In preferred embodiments, the membrane comprises slit pores. In some embodiments, the membrane further comprises at least one surface treatment. In other embodiments, the membrane further comprises at least one electric field generator, such that an electric field is produced in or around at least one pore; examples of electric field generators include but are not limited to electrodes. In some embodiments, the membrane further comprises at least one surface treatment. In some embodiments, the membrane further comprises at least one of a pump and an actuator. In preferred embodiments, the membranes of the present invention are configured to generate physiological ultrafiltration volumes at capillary perfusion pressure.

A. Materials

The membranes of the present invention include any membrane material suitable for use in filtering biological fluids, wherein the membranes can be associated with nanofabricated pores. Examples of suitable membrane materials are known in the art and are describe herein.

In some embodiments, the membrane material is synthetic, biological, and/or biocompatible (e.g., for use outside or inside the body). Materials include, but are not limited to, silicon, which is biocompatible, coated silicon materials; thus, materials include but are not limited to, silicon, polysilicon, silicon carbide, ultrananocrystalline diamond, diamond-like-carbond (DLC), silicon dioxide, PMMA, SU-8, and PTFE. Other possible materials include metals (for example, titanium), ceramics (for example, silica or silicon nitride), and polymers (such as polytetrafluorethylene, polymethylmethacrylate, polystyrenes and silicones).

B. Nanofabricated Pores

A membrane of the present invention comprises at least one pore, where pore shapes include but are not limited to linear, square, circular, ovoid, elliptical, or other shapes. In some embodiments, the membrane comprises more than one pore, where the pores comprise a single shape or any combination of shapes. In some embodiments, a membrane comprises more than one pore, where the pore sizes range from about 10 to about 100 microns in any dimension; the dimensions need not be the same in any particular pore shape, the pores may comprise a single size or any combination of sizes. Although it is not necessary to understand the mechanism of invention in order to practice it, and although it is not intended that the invention be limited to any particular mechanism, it is contemplated that slit-shaped pores are the preferred structure responsible for the filtration specificity of the kidney.

Experiments conducted during the course of the present invention showed that membranes having slit pores retain sufficiently large solutes but provide improved hydraulic permeability when compared to cylindrical pores. The round shape of pores in conventional polymer membranes provides a fourth-power dependence of the volumetric flow rate on the pore radius r:

$$\frac{Q}{A\Delta P} = \frac{N\pi r^4}{8\,\mu L} = \frac{\varepsilon r^2}{8\,\mu L} \quad (1)$$

where Q is the volumetric flow rate, ΔP is the hydrostatic pressure difference across the membrane, A is the membrane area, N is the number of pores per unit membrane area, μ is the viscosity, L is the length of the pore, and is the membrane porosity (pore area per unit membrane area). In contrast, the volumetric flow rate through a slit-shaped pore is given as:

$$\frac{Q}{A\Delta P} = \frac{Nwh^3}{12\,\mu L} = \frac{\varepsilon h^2}{12\,\mu L} \quad (2)$$

where w is the long dimension of the slit, h is the critical width s of the slit, and L is again the length of the pore. For membranes that have a critical dimension that is just able to retain albumin ($h_{crit}=2r_{crit}$), the volumetric flow rate through the membrane with slit-shaped pores will be 2.67 times larger than the flow rate through a membrane with cylindrical pores (assuming comparable porosity, pore length, and pressure driving force). In addition, the membrane with slit-shaped pores provides much less steric hindrance to the transport of important "middle molecules" such as $\beta_2$-microglobulin due to the weaker interactions in the slit geometry. For example, a molecule with a 10% smaller radius than the critical pore size will have a sieving coefficient of approximately 0.1 through the slit-shaped pore compared to a sieving coefficient of 0.01 for the membrane with cylindrical pores. At equivalent volumetric flow rates of 30 ml/min, this difference corresponds to a 10-fold larger clearance (3 ml/min versus 0.3 ml/min) for the membrane with slit-shaped pores. This difference increases to 26.7-fold for membranes with the same porosity, thickness, and pressure driving force due to the greater hydraulic permeability of the membrane with slit-shaped pores.

The membranes of the present invention having slit pores are not limited to having a particular slit pore size. In some embodiments, the size for each slit pore is approximately 40 μm in length (e.g., 0.m μl in length to about 100 μm in length, although other lengths are contemplated). The membranes are not limited to having thereon a particular number of slit pores. In some embodiments, the membrane has approximately $10^4$ slit pores (e.g., $10^2$ slit pores, $10^3$ slit pores, $10^4$ slit pores, $10^5$ slit pores, etc). In preferred embodiments, the number of slit pores on the membrane is sufficient to allow the membrane to generate physiologically ultrafiltration volume at capillary perfusion pressure. The membranes having slit pores are not limited to a particular porosity. In some embodiments, the porosity of the membranes is approximately 1% (e.g., 0.1%, 0.5%, 1%, 2%, 5%, 10%, 20%, etc.).

In some embodiments, the present invention provides a series of membranes comprising sparse arrays of monodisperse slit-shaped pores, manufactured, for example, using silicon bulk and surface micromachining techniques (see e.g., Fissell W H, et al., J Am Soc Nephrol 2002; 13:602 A; incorporated herein by reference in its entirety). In particular, the present invention provides membranes for ultrafiltration with well-defined, slit-shaped pores designed and assembled using silicon bulk and surface micromachining techniques followed by surface modification with poly (ethylene glycol) (PEG). In experiments conducted during the course of the present invention, hydraulic permeability of a prototype membrane was measured before and after 200 hours of perfusion with bovine serum albumin. Convective and diffusive transport across prototype membranes was quantified and compared with a state of the art polysulfone membrane using Ficoll 70, a polydisperse spherical polymer of epichlorohydrin and sucrose. Hydraulic permeability of unmodified prototype membranes exactly matched first-principles predictions for liquid flow. Pore size was further confirmed by observation of Knudsen flow for argon, nitrogen, and carbon dioxide. Hydraulic permeability of PEG-modified membranes was consistent with slight pore narrowing by the coating, and was unchanged by extended perfusion with albumin. The molecular weight at which the sieving coefficient for Ficoll was half-maximal (0.5) was around 18 kD, compared with less than 10 kD for a polysulfone membrane. As such, the membranes of the present invention yielded membranes capable of generating physiologically significant ultrafiltration volumes at capillary perfusion pressure. The membranes of the present invention are fundamentally enabling for wearable or implantable renal replacement.

In some embodiments, the sizes of the slit pores are highly uniform. For example, in some embodiments, the pores are micromachined such that there is less than 20% size variability, more preferably less than 10% size variability between the dimensions of the slit pores. In further embodiments, the sizes of the highly uniform slit pores are of approximate dimensions that are similar to the size of the glomerular slit diaphragm, or about 2-100 nm by 2-100 microns. In such embodiments, it is contemplated that the pores permit ultrafiltration at in vivo pressures (e.g., systolic blood pressure) (e.g., capillary perfusion pressure). Additionally, it is contemplated that such pores permit size selective exclusion of undesired molecules within specific size restrictions.

Pressure driven ($\Delta P$) flow Q of incompressible fluid of viscosity $\mu$ through a narrow pore or pipe of rectangular cross section w×h and length L where h<<w is described by:

$$Q = (wh^3/12 \mu L) \Delta P$$

And thus flow per unit area $Q_A$ of pore w×h is given by $$Q_A = (h^2/12 \mu L) \Delta P$$

Pressure driven ($\Delta P$) flow Q of incompressible fluid of viscosity $\mu$ through a narrow pore or pipe of round cross section of diameter h and length L is described by $$Q = [\pi (h/2)^4/8 \mu L] \Delta P$$

or $$Q = (\pi h^4/128 \mu L) \Delta P$$

And thus flow per unit area $Q_A$ of a round pore of area $\pi(h/2)_2$ is given by $$Q_A = [(h/2)^2/8 \mu L] \Delta P$$

or $$Q_A = (h^2/32 \mu L) \Delta P$$

Thus for a given critical dimension h of a pore, a rectangular cross section pore with minimum dimension h has a higher hydraulic permeability per unit area than does a round pore of diameter h, by a factor of 2.6

Factors that determine appropriate pore size and shape include a balance between hydraulic permeability and solute permselectivity. It is contemplated that a slit shape is an optimal shape, although the present invention is not limited to slit shapes.

In preferred embodiments, the slit pores are created by micromachining (referred to as "nanofabrication") techniques. Micromachining is a process that includes photolithography, such as that used in the semiconductor industry, to remove material from, or to add material to, a substrate. These techniques are well known (see, for example, Park, B et al. (2002) Med Device Technol 13(2): 32-34; Voldman, J et al. (1999) Annu Rev Biomed Eng 1: 401-425; and Wagner, B (1995) Endosc Surg Allied Technol 3(4): 204-209; Encyclopedia of Chemical Technology, Kirk-Othmer (1995), Volume 14, pp 677-709; Rierret, R F (1996) Semiconductor Device Fundamentals (Addison-Wesley); and Van Zant (1997) Microchip Fabrication $3^{rd}$. edition (McGraw-Hill); Petersen, K E (1982) Proceedings of the IEEE 70:420-457; Roy S, and Mehregany M (1999) Introduction to MEMS, in Microengineering Aerospace Systems (eds: Helvajian H; The Aerospace Press; El Segundo, Calif.) pp. 1-28., and U.S. Pat. No. 6,044,981; each of which are incorporated herein by reference in their entireties). Although not specifically limited, in preferred embodiments, 1 mm×1 mm nanoporous membranes are generated having thereon approximately $10^4$ 40 µl-long slit pores, with an overall porosity of approximately 1%. In preferred embodiments, the nanoporous membranes of the present invention resemble the filtration specificity of the kidney, and represent an improvement over existing membranes having non-slit shaped pores (e.g., the membranes are able to retain sufficiently large solutes but provide improved hydraulic permeability when compared to cylindrical pores).

C. Additional Components

1. Surface Treatments

In some embodiments, the membrane further comprises at least one surface treatment or modification. In some preferred embodiments, the surface treatment or modification promotes attachment of specific animal cells to the membrane, promotes attachment of desirable proteins, inhibits undesirable protein deposition on the membrane, or inhibits blood coagulation on or in the vicinity of the membrane. Such treatments or modifications may include but are not limited to patterned or unpatterned adsorption or covalent linkage to the membrane surface of RGD peptide moieties, integrins, fibronectin, laminin, collagens, oligosaccharides, or polyethylene glycol moieties. Particular cells or molecules attached to or located at the membrane surface and/or within the pores may be used to render the porous membrane more biocompatible, less thrombogenic, or may be used to alter the filtration characteristics of the pores. Furthermore, the cells may be used to process or modify the filtrate produced by the membrane. In some embodiments, modification of the pores includes but is not limited to covalent attachment of peptides or proteins, either alone or selected to promote attachment of cells such as endothelial or epithelial cells. Methods to modify silicon and silicon compounds to promote cell attachment or to retard cell attachment are well known (see, for example, Whitesides et al. (1996) PNAS 93: 10775-10778 for cell attachment; and Whitesides et al. z91997) Exp Cell Research: 305-313 for patterned attachment; each herein incorporated by reference in their entireties).

In some embodiments, the surface of the nanoporous membranes of the present invention are modified with polyethylene glycol (PEG) or related compounds (e.g., oligosaccharide surfactant polymer monolayers). The present invention is not limited to a particular method for modifying nanoporous membrane surfaces with PEG (see, e.g., Papra A, et al., Langmuir 17:1457-1460 (2001); incorporated herein by reference in its entirety). Grafting of polyethylene glycol (PEG) monolayer coatings to enhance biofouling resistance of inorganic substrates such as glass and silicon has been investigated. Two surface modification strategies have been established: (1) a multi-step non-aqueous solution synthesis; and (2) a chemical vapor deposition (CVD) method. The CVD route uses a heated stream of ethylene oxide (EtO) with boron trifluoride ($BF_3$) as a catalyst in a nitrogen carrier gas stream. The surface is first pretreated with 3-aminopropyltrimethoxysilane to form a uniform surface coating with free amine groups. The CVD reaction takes place at the free amine groups and provides a uniform coating suitable for nanoscale features. The solution based PEG attachment is a multi-step synthesis that involves the conversion of PEG to PEG-O—$SiCl_3$ as a reactive intermediate, which is then coupled with free surface Si—OH groups. The surface concentration of the silanol groups is enhanced by a pretreatment of the surface with a piranha solution (1:3 $H_2O_2$:conc. $H_2SO_4$ v/v). Modification of the nanoporous membrane surfaces with PEG reduced protein fouling (e.g., the PEG coating limited albumin adsorption, and reduced thrombosis initiation) (see, e.g., Sharma and Desai, Journal of Nanoscience and Nanotechnology, 2005, 5(2); Popat and Desai—Biosensors and Bioelectronics, 2004, 19(9); Fissell, et al., American Journal of Physiology—Renal Physiology, Vol. 293, 2007, p. 1209).

2. Electric Field Generators

In preferred embodiments, the membranes have one or more electric field generators associated with them, such that an electric field is produced in or around the pores. The electric field is used, for example, to control and adjust the relative contributions of electrostatic charge and steric hindrance across a pore.

In some embodiments, an electric field is created in and around pores of a membrane by any of several means; this means include, but are not limited to, electrodes. The electrodes may be located within the pores, or on either side of the pores, or on the surface of the membrane in which the pores are fabricated.

The electrodes may be formed by well-known semiconductor processing techniques from conductive materials, such as pure metals or alloys, or other materials that are metallic conductors. Examples include but are not limited to aluminum, carbon (such as graphite), cobalt, copper, gallium, gold, indium, iridium, iron, lead, magnesium, mercury (such as amalgam), nickel, niobium, osmium, palladium platinum, rhenium, rhodium, selenium, silicon (such as highly doped polycrystalline silicon), silver, tantalum, tin, titanium, tungsten, uranium, vanadium, zinc, zirconium, platinum, palladium, iridium, or any combination or alloys of these metals; noble metals and their alloys are unreactive in biological systems. The thickness of the electrodes may range from about 10 nm to about 1 um; in some embodiments, the electrodes are about 10 nm to about 1 mm; in other embodiments, they are about 20 nm to about 100 um; in other embodiments, they are about 25 nm to about 1 um thick. Within a membrane, the electrodes may be fabricated of the same or different materials, and they may be the same size or different sizes.

Other means for generating a useful electrostatic field include but are not limited to grafting polymers, electret deposition and polarization, attachment of proteins and polymers which are negatively charged at physiologic pH (approximately 7.00-7.50).

3. Pumps

Fabrication of the pores by well known MEMS techniques lends itself to the integration of such a membrane with previously realized pumps, electrokinetic pumps, pressure sensors, valves, etc. Thus, in some embodiments, the present invention also provides a system as described below, where the membrane and/or system further comprises microscopic peristaltic pumps, configured to direct the movement and flow of fluids. The pumps are generated by nanofabrication with "soft lithography," using techniques known in the art.

4. Actuators

The use of silicon micromachining techniques lends itself to the addition of devices to monitor or clean the membrane by thermal, acoustic, electrical or mechanical means. Thus, in some embodiments, the present invention also provides a system as described below, where the membrane and/or system further comprises actuators.

In the system of the present invention as described above, the nanoscale actuators and electronic elements incorporated during nanofabrication are utilized together to limit or reverse protein fouling of the pore, permitting prolonged or indefinite service lifetimes for a filtration device.

5. Monitoring and Control Systems

The systems and devices of the present invention may employ hardware and/or software monitoring and control systems that collect data, analyze, and report on one or more operations of the system or device and/or one or more physiological characteristics of the subject being treated. In some embodiments, the monitoring and control system regulates the operation of the devices/system. The control system may comprise any combination of software or hardware to carry out its functions. These may be included in the device or as part of a separate device.

For example, in some embodiments, the control component is used in conjunction with implanted devices to control fluid conduits having actively regulated conduit diameters for real-time control of resistance to fluid flow and hydrostatic pressure in the hemofilter and bioreactor. Integrated fault sensing and safety controls may be used to isolate the device from the vasculature in the event of a membrane failure or other problem.

The control component may also be used to control/monitor extracellular fluid volume. Control of extracellular fluid volume can be broken down into three tasks: ECF sensing, selection of feedback algorithm, and effector mechanism. In hemodialysis, ECF volume is sensed by weighing the patient and by physical examination. In an implantable device, this information and be used or supplemented with hemodynamic monitoring, including arterial and venous pressure waveform analysis and bioimpedance measurements. For example, a patient may enter his or her weight through a patient data interface, and a computerized algorithm programs the device to divert a volume of ultrafiltrate from the bioreactor directly to a urinary collection system, be it a bladder anastamosis or a collection pouch. In some embodiments, as the bioartificial kidney may have direct connections to the arterial and venous vasculature, real-time arterial and venous pressure waveform monitoring is used, with programmed ultrafiltrate diversion to control ECF volume. A patient interface may use principles commonly used with pacemakers and AICDs (automatic implantable cardio-defibrillators).

II. Systems

The present invention also provides a system comprising a compartment and the porous membrane of the present invention as described above (e.g., a nanoporous membrane having slit pores and a PEG surface coating), where the porous membrane is supported within the compartment of a device, such that the presence of the membrane separates the compartment into two sub-compartments. In some embodiments, the system is a device with a housing, where the housing defines the outer surfaces of the compartments. A housing may be composed of any desired material. Where the system is used on or in a subject, the housing is preferably made of or coated with a biocompatible material.

The compartment is of any appropriate shape and configuration such that the membrane within the device compartment forms two sub-compartments that are completely separate from each other, except that a first sub-compartment is in fluid connection with a second sub-compartment only by means of the pores within the membrane. In preferred embodiments, the device further comprises means for permitting entry into the first sub-compartment of a first fluid to be filtered (e.g., a feed fluid), and a means for permitting exit of excess feed fluid after filtration or of retentate, where the retentate did not get filtered through the membrane. In some embodiments, the device further comprises means for permitting exit of a second fluid from the second sub-compartment, where the second fluid is an "ultrafiltrate" or "permeate" generated from the feed fluid by means of the pores of the membrane, and optionally means for entry into the second sub-compartment of a third fluid, where such third fluid is a dialyzing fluid for the feed fluid.

Means for permitting entry of fluid into the first and second sub-compartments include but are not limited to an opening in the housing, on one side of the membrane; if such means in both sub-compartments comprise an opening, then one opening is in either side of the membrane. The opening may be of any suitable configuration, including but not limiting spheroid, elliptical, and slit-like. Means for permitting exit of fluid from the first and the second sub-compartments include but are not limited to the means for permitting entry of fluid as described above. The entry and exit means are suitably positioned in the housing to allow entry of fluid, filtration, and exit of fluid, from either or both sub-compartments. The entry and exit means may further comprise conduits for delivering fluid to the sub-compartments; such conduits include but are not limited to tubing. When present, such tubing may be inserted into the entry and or exit means, or they may be attached to the entry and/or exit means in any fashion, such as by a clamp or threaded connection, which forms a fluid-tight seal of the tubing with the entry and/or exit means.

In further embodiments, the membrane of the device of the invention as described above further comprises at least one surface treatment, as described above. In some embodiments, the surface treatment comprises attaching cells to the surface of the membrane, as described above. In these embodiments, it is contemplated the membrane is used as a scaffolding for cells to process the permeate, for example as is described in U.S. Pat. Nos. 5,549,674, 5,686,289, 6,060,270, 6,150,164, and 6,410,320, the disclosures of which are incorporated herein by reference in their entireties.

In other further embodiments, the membrane of the device of the invention as described above further comprises means for generating an electrostatic field, as described above. If desired, the device may further comprise electronic components, for example, amplifiers, filters, transmitters and/or signal preconditioning components. In some embodiments, such components can be incorporated onto the surface of the membrane. In particular, if the membrane comprises elemental silicon, well known integrated circuit technology may be used to place all the circuitry in miniaturized form on a single chip, which is incorporated into the membrane or placed onto and/or attached to the surface of the membrane.

In yet other further embodiments, the membrane of the device of the invention as described above further comprises at least one surface treatment (e.g., with PEG), and at least one means for generating an electrostatic field.

III. Uses

The membranes of the present invention (e.g., a nanoporous membrane having slit pores and a PEG surface coating) are able to filter any fluid from which it is desired to filter one or more types of molecules. The size, shape, array pattern, and charge across a pore are selected in accordance with the molecules to be filtered. Fluids that can be filtered include but are not limited to biological fluids, including blood and plasma. Illustrative, non-limiting uses are described below to highlight the flexibility of the present invention.

A. Hemofiltration

The kidney's functional unit, the nephron, provides for elimination of wastes and toxins without the need for specific enzymes and transporters for each toxin. All but the large proteins and cellular elements in the blood are filtered; a system of cells then reclaims specific filtered substances needed by the body, and allows all others to pass as urine. Filtration is accomplished by the glomerulus, a tuft of capillaries supported by a basement membrane and specialized epithelial cells called podocytes. The filtrate is then passed to the renal proximal tubule, a hollow tube of cells surrounded by capillaries, which accomplishes the bulk of reclamation, as well as other metabolic functions, including excretion of acid as various products.

In preferred embodiments, the ultrafiltration devices of the present invention having nanoporous membranes (e.g., a nanoporous membrane having slit pores and a PEG surface coating) are used for hemofiltration. In preferred embodiments, such ultrafiltration devices having, for example, nanoporous membranes with slit pores and a PEG surface coating reproduce the filtration functions of the native kidney.

In operation, blood is directed from a patient's vasculature, in either an extra- or intra-corporeal circuit, into the first sub-compartment of the device. After the blood is filtered, it exits the first sub-compartment, and is returned to/is directed back into patient's vasculature. The route of the blood from the patient through the device and back into the patient is referred to as the "blood flow." In some of these embodiments, the blood flow may be assisted or directed by pumps. In some of these embodiments, an ultrafiltrate free of proteins is formed by hydrostatic pressure of blood against the membrane. In some of these embodiments, the ultrafiltrate fills the second sub-compartment during filtration, and then exits the sub-compartment. In some embodiments, the exit means for the ultrafiltrate include but are not limited to extraction and draining, where draining may be either by active or passive means. In yet additional embodiments, the ultrafiltrate may be channeled to further devices, which include but are not limited to testing devices and bioreactors, or it may be removed for disposal. Removal may be either intracorporeally, as for example by diversion to the bladder, ileal pouch, or other anatomic conduit, or extracorporeally, as to an external pouch.

In some of these embodiments, the membrane pores, and/or either or both surfaces of the membrane itself, are kept free of debris by electrostatic or electromechanical devices as described above. The membrane is kept free of debris either by preventing the debris from accumulating on the surface, as for example via the PEG surface coating, and/or by maintenance of a steady electrical current, or by removing accumulated debris, as for example by administering intermittent electrical current or pulses of current, which may also, in turn, excite an actuator.

By means of the device of the present invention as described above, the device mimics the native filtration function of the kidney by producing an ultrafiltrate of plasma similar to that produced by a kidney. Moreover, the ability to prevent fouling of the membrane (e.g., via the PEG membrane surface coating) results in a long service life from the membrane, such that the membrane can be incorporated within a permanent implantable artificial kidney.

Other filtration applications to which it may be suited are also contemplated.

B. Diagnostic Uses

The ultrafiltration devices of the present invention also find use in diagnostic applications. For example, the devices provides a means for selectively screening out undesired molecules (e.g., proteins) within fluids, such that a particular analyte to be analyzed (e.g., small molecules such as glucose, electrolytes, ions, etc.) in the absence of interfering molecules. For example, present electrochemical sensors for glucose measurement are severely hampered by protein fouling of the sensor, and great effort is devoted to the invention of fouling retardants to prolong sensor life. An ultrafiltrate substantially free of proteins, but still containing smaller constituents of blood, including but not limited to sodium, potassium, chloride, glucose, provides a solution to assay for glucose concentration without protein fouling.

The device may be used to detect any desired analyte. In some embodiments, the analyte is a small molecule. In other embodiments, the analyte is a pathogen or a molecule or molecular complex associated with the presence of a pathogen in a sample (e.g., in a blood sample).

In some embodiments, the diagnostic devices are applied on or in a subject for monitoring the presence of or amount of an analyte of interest. For example, a glucose or electrolyte sensor monitors (e.g., at one or more time points or continuously) blood analyte levels. A processor associated with the device reports this information to the subject or to the appropriate medical personnel (e.g., by displaying the analyte concentration or by transmitting the analyte concentration—e.g., to a computer, PDA, phone, or other device). In some embodiments, the processor triggers, where appropriate, release of a drug or other substance (e.g., insulin) based on the measured concentration so as to alter the physiology of the subject appropriately. In some embodiments, changes in analyte concentration are measured in response to changes in the environment (e.g., ambient environment, diet, etc) or upon administration of test compounds (e.g., drugs) to the subject (e.g., for testing the safety or efficacy of drugs).

In other preferred embodiments, the device is associated with another medical device (e.g., a catheter) that is used for in vitro or in vivo detection of the desired analyte. The sensors of the present invention, provide over existing sensor technology (e.g., U.S. Pat. No. 6,405,066, herein incorporated by reference in its entirety).

C. Bioreactors

In some embodiments, the system is used as a convectively fed bioreactor for cell growth and tissue engineering, for example, as described in U.S. patent application Ser. No. 09/949,575 (Humes et al.), the contents of which are herein incorporated by reference in their entirety. In some such embodiments, cells or tissues are applied to a surface (e.g., a membrane, a chamber surface) or are maintained in suspension in a chamber, such that one or more desired fluid flows from the system are exposed to the cells (e.g., exposure of filtered or unfiltered biological fluids to the cells). In some embodiments, the system is configured to permit the exposure of synthetic growth media (e.g., with or without serum) to the cells, alone, or in combination with filtered or unfiltered biological fluid. In some embodiments, the cells are transgenic cells. In some embodiments, the system is used as a screening system to select cells, genes, drugs, proteins, and/or growth conditions with desired characteristics and properties.

The cells or tissues may also be used to express or provide one or more desired factors to a filtered biological fluid that is to be returned to a subject or otherwise manipulated or analyzed.

IV. Bioartificial Organs

The present invention also provides bioartificial organs for in vivo or extracorporeal uses. In some embodiments, the bioartificial organs comprise cells attached to or associated with a surface of a device. In some such embodiments, the surface is modified (e.g., modified with PEG) to control the biological activity of the attached or associated cells. In some preferred embodiments, the surface is a membrane of the present invention, having slit pores, as described herein (e.g., a nanoporous membrane having slit pores and a PEG surface coating). However, the present invention is not limited to the use of surfaces that comprise the membranes of the present invention. In preferred embodiments, the devices are configured to combine hemofiltration with cell therapy in a manner that mimics or supplements the function of a healthy organ.

In some embodiments, the cells of the bioartificial organ are supplied with nutrients by an ultrafiltrate stream generated by ultrafiltration of blood or body fluids by a membrane of the present invention. In other embodiments the cells and tissues of the bioartificial organ are grown on or attached to a membrane of the present invention. In other embodiments the cells and tissues of the bioartificial organ are grown on or attached to a membrane of the present invention and the cells of the bioartificial organ are supplied with nutrients by an ultrafiltrate stream generated by ultrafiltration of blood or body fluids by a second membrane of the present invention.

In preferred embodiments, the bioartificial organ is a bioartificial kidney. Such devices, find use, for example, in the treatment of end-stage renal disease. The compact nature of the devices of the present invention allows for in vivo or easy, portable, extracorporeal treatment. In-center dialysis, the most common mode of treatment of end-stage renal disease, is expensive and labor-intensive. Thus, the miniature devices of the present invention simplify, improve, or relocate to home or in vivo, the treatment of end-stage renal disease, resulting in cost savings and improved quality of life for treated subjects. Thus, the present invention provides advantages over or extensions to existing bioartificial kidneys (see e.g., U.S. Pat. No. 6,150,164, herein incorporated by reference in its entirety).

A. Surfaces

In some embodiments, the devices comprise a surface for the growth of cells (see e.g., section III, C above describing bioreactors). The present invention is not limited by the nature of the surface on which the cells are grown. Any surface that permits cell to have desired biological properties (e.g., attachment, growth, cell division, protein production, protein secretion, membrane fluidity, endocytosis, etc.) is contemplated by the present invention. The material properties upon which cells are grown influence cell attachment and differentiation. This includes geometric patterning and distribution of ECM binding proteins, surface topology, and porosity of the surface. In some embodiments, the surfaces are coated with self-assembling monolayers, multilayers, or particles. A wide variety of patterned self-assembling materials are known (see e.g., Mrksich, Chem. Soc. Rev., 29:267 (2000) and U.S. Pat. No. 6,017,390). The coating used on the surfaces can comprise or provide and attachment site for ligands for selective protein/cell attachment or rejection, or otherwise selectively attract or reject desired or undesired molecules or materials.

Examples of surface modification that allow one to tailor the properties of the associated cells are found in Desai, Med. Eng. Phys. 22:595, 2000, Deutsch et al., J. Biomed. Mater. Res., 53:267, 2000, Kapur et al., J. Biomed. Mater. Res., 33:205, 1996, Brunette and Chehroudi, 121:49, 1999, Brunette, Exp. Cell Res., 167:203, 1986, Brunette, Exp. Cell Res. 164:11, 1986, den Braber et al., J. Biomed. Mater. Res., 29:511, 1995, den Braber et al., J. Biomed. Mater. Res., 17:2037, 1996, Curtis and Wilkinson, Biomaterials 18:1573, 1998, Craighead et al., Biomed. Microdevices, 1:49, 1998, Mata et al., Biomed. Microdevices 4:267, 2002, Mata et al., J. Biomed. Mater. Res., 62:499, 2002, and U.S. Pat. Nos. 5,776, 748, 5,843,741, 5,976,826, 6,569,654, 5,770,193, 5,759,830, 5,736,372, and 5,770,417, each of which is herein incorporated by reference in their entireties.

In some preferred embodiments, the surface is a membrane of the present invention (see e.g., section I, above) (e.g., a nanoporous membrane having slit pores and a PEG surface coating). Use of such membranes provides a number of advantages, including the ability to miniaturize the bioartificial device to allow in vivo use or efficient and convenient extracorporeal use. An example of a nanoporous membrane for use in the bioartificial organs of the present invention is described in the Examples.

The surface of may be precoated with suitable extracellular matrix (ECM) components including Type I collagen, Type IV collagen, laminin, Matrigel, proteoglycan (such as heparin sulfate and dermatan sulfate) fibronectin, and combinations thereof to form an ECM layer. Once an ECM layer has been established on the surface, this layer is then seeded with desired cells.

B. Cells

A variety of cells find use in the bioartificial organs of the present invention. In some embodiments the cells of the bioartificial organ are liver, duodenal, intestinal, gastric, pancreatic, thyroid, parathyroid, adrenal, gonadal, pituitary, or hypothalamic cells. In some embodiments the cells of the artificial organ are bone marrow cells. In other embodiments the cells of the bioartificial organ are stem cells, feeder cells, or other precursor cells. In still other embodiments, the cells of the bioartificial organ are derived from stem or precursor cells. In still other embodiments, the bioartificial organ comprises cells that induce the differentiation of nearby cells or attract nearby cells to the organ. In some embodiments, the cells comprise one or more transgenes (e.g., having inducible promoters).

In preferred embodiments, the cells are from kidney or associated tissue. Cells from many segments of the nephron have been grown in primary culture (see for example, Handler & Burg in "Application of tissue culture techniques to study of renal tubular epithelia" in Windhager & Giebisch (eds): Handbook of Physiology, Section 8, Renal Physiology, American Physiological Society, Williams & Wilkins, Baltimore; incorporated herein by reference in its entirety). Specific cells have been separated on the basis of differential growth, by mechanical dissection, by differential centrifugation and with the aid of specific antibodies (immunodissection).

In some preferred embodiments, the cells are renal proximal tubule cells. These cells replace the metabolic, endocrine, and immunologic functions of a damaged kidney. Cells are grown on the appropriate surface and then exposed to ultrafiltrate. The cell-exposed ultrafiltrate is then returned to a subject. It is contemplated that the cell-exposed ultrafiltrate contains serum appropriate levels of desired biological components (e.g., 1,25 dihydroxy-vitamin $D_3$, sodium, glucose, etc.).

In some embodiments, a mixture of cell types is associated with the surface. In some such embodiments, a first layer of a first cell type is grown, which provides a new surface for the growth a second or additional cell types. For example, pericyte, vascular smooth muscle or mesangial cells can be first seeded on a ECM layer and allowed to reach confluence. Thereafter, endothelial or other cells can be seeded. Pericyte cells are described by Sims in Can. J. Cardiol. 7(10):431-443 (1991) and Shepro et al in FASEB J. 7:1031-1038 (1993), incorporated herein by reference. Mesangial cells, the preferred type of pericyte cell, are described by Davies in Kidney International, 45:320-327 (1994), incorporated herein by reference.

Suitable culturing techniques useful for seeding these cells on the surface are described by Scott et al., J. Cell Sci. 105: 269-273, 1993; Schneider et al., Surgery 103:456-462, 1988; Kadletz et al., J. Thoracic and Cardiovascular Surgery 104: 736-742, 1 1992; Shepard et al., Surgery 99: 318-3.about.6, 1986; and Demetriou et al., Science 23:1190-1192, 1986; each of which is incorporated herein by reference in their entireties.

EXAMPLES

The following examples are provided in order to demonstrate and further illustrate certain preferred embodiments and aspects of the present invention and are not to be construed as limiting the scope thereof.

Example 1

Nanofabrication of Membranes

This example describes the process flow for fabrication of nanoporous membranes; this process is depicted in FIG. 1. The starting substrate is a 400 μm-thick, 100 mm-diameter, double side polished (100)-oriented silicon wafer that is obtained from a commercial vendor of semiconductor substrates. The wafer is coated with a 5000 Å-thick layer of low-stress silicon nitride (LSN) by low-pressure chemical vapor deposition (LPCVD). Next, a 4 μm-thick film of polysilicon is deposited by LPCVD (FIG. 1(a)) and followed by thermal oxidation to grow a 2500 Å-thick layer of $SiO_2$. The oxide layer on the wafer front side is then patterned by photolithography and wet etching in buffered hydrofluoric acid (BHF) to create an etch mask, which is used to pattern the underlying polysilicon film by reactive ion etching (RIE) in chlorine plasma. Afterwards, BHF is used to remove the masking oxide on both wafer front and back sides and followed by RIE to remove polysilicon on the wafer back side (FIG. 1(b)). Next, thermal oxidation is performed to realize a 20 nm-thick $SiO_2$ film that will define the pore size in the nanomembrane (FIG. 1(c)). It should be noted that other pore sizes, if desired, could be realized by varying the thickness of the $SiO_2$. The anchor regions are then defined by selectively patterning the oxide on the wafer frontside using photolithography and BHF. Next, another 4 mm-thick polysilicon film is deposited by LPCVD (FIG. 1(d)) and followed by global planarization by chemical-mechanical polishing (CMP) to remove any excess polysilicon and expose the pore regions on the frontside (FIG. 1(e)). The polysilicon and LSN on the backside are then removed by RIE in chlorine and SF6 plasma, respectively, and followed by a LPCVD deposition of LSN on both front and back sides of the wafer (FIG. 1(f)). Afterwards, the LSN on the wafer backside is patterned using photolithography and RIE to define an etch mask (FIG. 1(g)) for the subsequent KOH etch to create suspended membranes (FIG. 1(h)). Finally, the masking LSN and $SiO_2$ films are etched in concentrated hydrofluoric acid to realize the nanoporous membranes (FIG. 1(i)).

Figure 2:
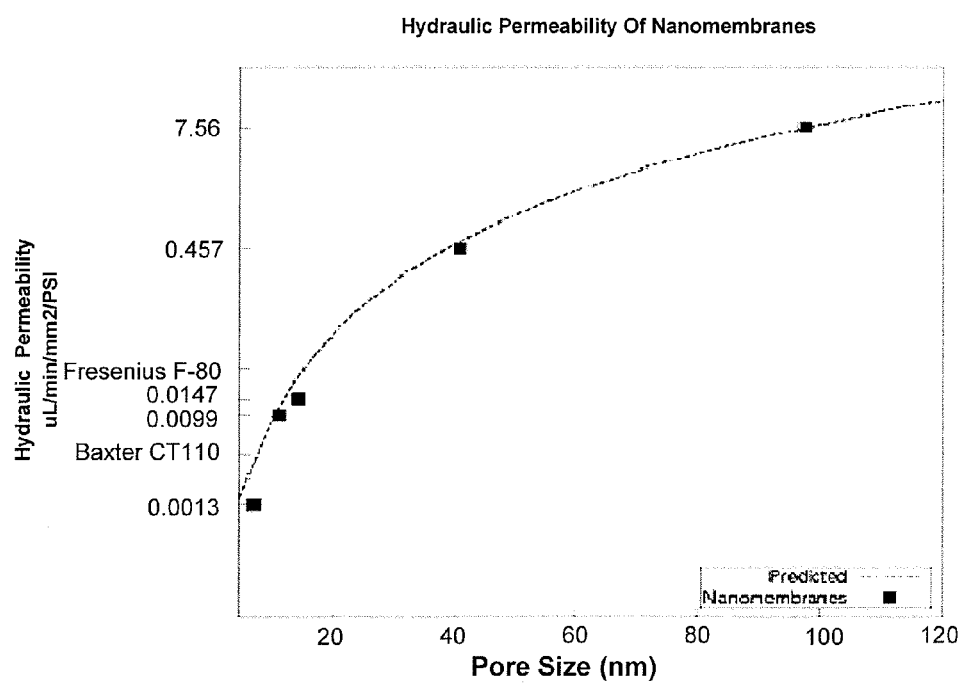
FIG. 2 shows a graph of hydraulic permeability of nanofabricated membranes of the present invention, with hydraulic permeabilites of two commercial polymer dialysis membranes (Baxter CT110 and Fresenius F-80) plotted for comparison.

In additional experiments, the design and construction of polysilicon membranes with 10 to 100 nm pores was characterized. The nanoporous membranes were fabricated by standard silicon bulk and surface micromachining processes. The pore structure was defined by deposition and patterning of a polysilicon film on the silicon wafer. The critical submicron pore dimension is defined by the thickness of a sacrificial $SiO_2$ layer, which was grown with unprecedented control to within +/−1 nm. The oxide layer was etched away in the final processing step to create the porous polysilicon nanomembrane. Membranes were mounted on polycarbonate filter inserts and examined under light microscopy for breaks or pinholes. Carriers were inserted into an Ussing chamber device fitted with pressure transducers, and both sides of the membrane were primed with aqueous solution. One side of the chamber was connected to a collection vessel at atmospheric pressure, and the other to a calibrated syringe. Syringe pumps were used to deliver fluid at set rates to the membrane, and the pressure generated by flux through the membrane was measured. Agreement was obtained between the observed and predicted hydraulic resistance. The hydraulic permeability was similar to that of commercial ultrafiltration membranes, suggesting that repeatable pressure-driven hydraulic flows may be observed in micro- and nano-machined membranes (FIG. 2).

Example 2

Extracorporeal Hemofiltration

Figure 3:
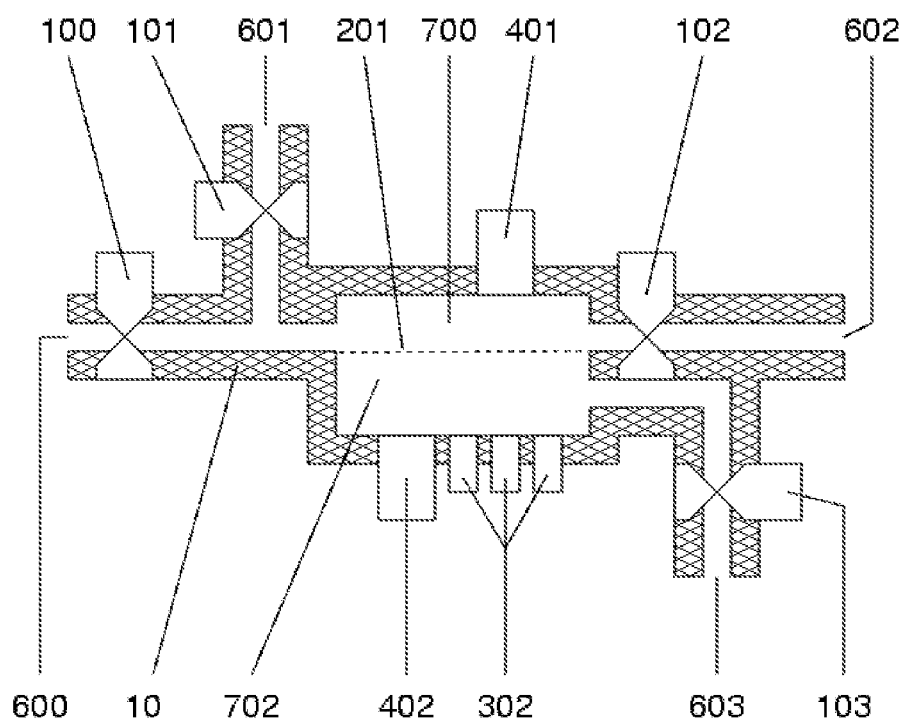
FIG. 3 shows an extracorporeal hemofiltration device in some embodiments of the present invention.

This example demonstrates how a nanofabricated nanoporous membrane may be used to form an extracorporeal hemofiltration device (see e.g., FIG. 3). Blood from a patient or from a stored supply is directed to an orifice 600 by means of a cannula, catheter or other means. An optional pump 100, which may be peristaltic, rotary, roller, or other, is used to regulate a flow of blood to a chamber 700, which contains a pressure sensor 401 and is bounded by a membrane 201 composed of a plurality of pores. Said pores may be shaped to optimize hydraulic permeability, and may be all alike or dissimilar. Furthermore, said pores may contain or comprise electrodes, surface treatments, or be coated with chemicals, polymers, proteins, sugars, and the like to impart a particular electrostatic charge to the pore or a region around the pore, and impart an electric field within the pore. Blood exits the chamber 701 via an orifice 602 with an optional pump 102 which may be peristaltic, rotary, roller, or other, and is returned to the patient or to a reservoir via cannula, catheter or other means. Fluids, in this example an electrolyte solution, or optionally an anticoagulant solution, or other solution not specified may be introduced into the blood in chamber 701 via orifice or inlet 602 and optional pump or valve 101. The pressure sensor 401, in combination with external or integrated electronics and controls, with valves and pumps 100, 101, and 102 may be used to regulate flow of blood into and out of chamber 701, and specifically to regulate and adjust the hydrostatic pressure in chamber 701. A second chamber 702 is positioned to receive filtrate passing through the membrane 201 either under force of hydrostatic pressure or eletroosmotic flow or other means not specified. Chamber 702 incorporates a second pressure sensor 402, a sensor or array of sensors 302 incorporating but not limited to optical, conductance, impedance, magnetic resonance, electrochemical, or immunologic principles, and a conduit 603 and pump or valve 103 for removal of fluid to a reservoir or drain. The sensor or array of sensors 302 may be used to monitor the composition of the ultrafiltrate and actuate alarms, valves, or other devices, including but not limited to telemetry and telephony devices, in event that a parameter measured of the ultrafiltrate falls out of a prescribed range. In this fashion a nanofabricated nanoporous membrane may be used to accomplish hemofiltration of blood.

Example 3

Continuous Blood Glucose Sensor

Figure 4:
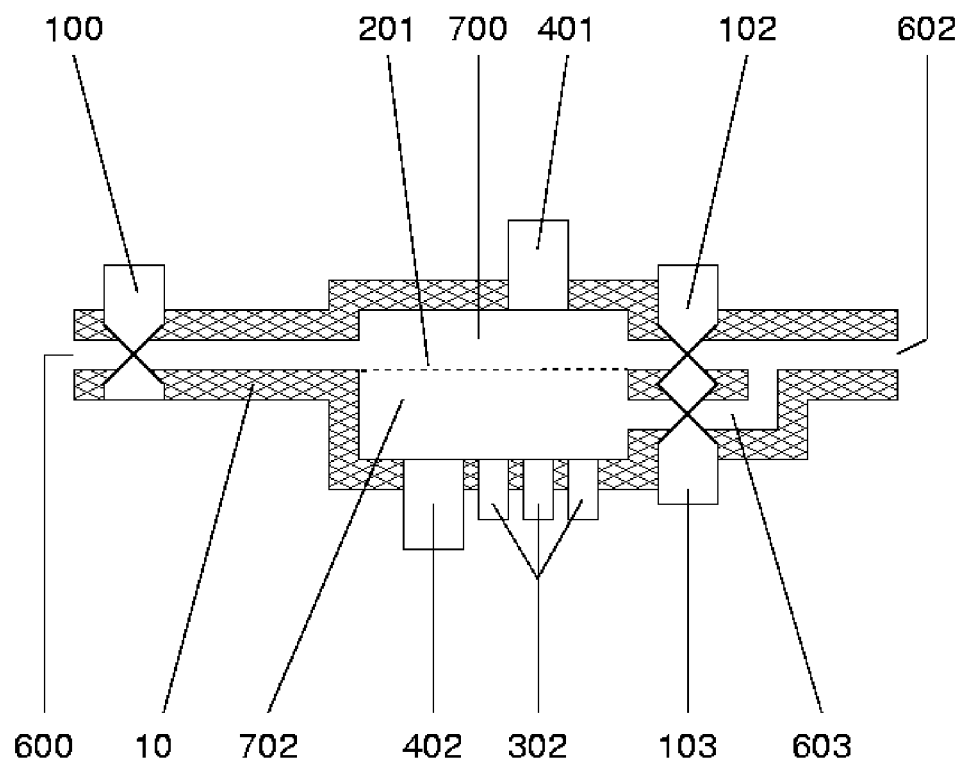
FIG. 4 shows a continuous analyte sensor in some embodiments of the present invention.

This example demonstrates how a membrane may be used to form a continuous blood glucose sensor. The novelty and advantage of this approach is the rapidity with which the glucose level in the blood is transmitted to the sensor, as glucose is carried by convection to the sensor, rather than by diffusion towards the sensor, while still affording the sensor protection from elements in the blood that may be injurious to or degrade the sensor. The example of a blood glucose sensor is not to be construed as limiting the application; it may be applied to the analysis of cell and/or protein free fluids for arbitrary analytes by arbitrary means. A preferred embodiment is illustrated in FIG. 4. Blood from the patient is directed by means of a cannula, a vascular anastamosis, a synthetic graft, or other means to an inlet 600 optionally equipped with a pump or valve or other flow controller 100 to a chamber 700, which optionally contains a pressure sensor 401 and is bounded by a membrane 201 composed of a plurality of pores. Said pores may be shaped to optimize hydraulic permeability, and may be all alike or dissimilar. Furthermore, said pores may contain or comprise electrodes, surface treatments, or be coated with chemicals, polymers, proteins, sugars to impart a particular electrostatic charge to the pore or a region around the pore, and impart an electric field within the pore. A second cannula or vascular anastamosis, or synthetic graft or other means returns blood from the chamber via an optional flow controlling device 102 and outlet 602 to the patient's blood stream. The pressure sensor 401, in combination external or integrated electronics and controls, with valves and pumps 100 and 102 may be used to regulate flow of blood into and out of chamber 700, and specifically to regulate and adjust the hydrostatic pressure in chamber 700. A second chamber 702 is positioned to receive filtrate passing through the membrane 201, and optionally incorporates a second pressure sensor 401, and a sensor or array of sensors 302 incorporating but not limited to optical, conductance, impedance, magnetic resonance, electrochemical, or immunologic principles. In the present Example, at least one of the sensors 302 is able to measure the concentration of glucose in the ultrafiltrate. The ultrafiltrate then exits the second chamber, either under hydrostatic pressure or by means of an active pump or valve 103 and is directed to an outlet 603 which joins with and is continuous with outlet 602 returning blood from the first chamber 700 to the patient's blood stream by means of a cannula or vascular anastamosis, or synthetic graft or other means. The sensor or array of sensors 302 may be used to monitor the composition of the ultrafiltrate and actuate alarms, valves, or other devices, including but not limited to telemetry and telephony devices, in event that a parameter measured of the ultrafiltrate falls out of a prescribed range. In the present example, the sensor would be connected to central processing unit incorporating a digital-to-analog converter and a means, such as an antenna or a light emitting device (LED) for transmitting the value measured by the sensor through the patients skin by electromagnetic or optical means, for detection, recording, and analysis by the patient or others. In this way, the invention may be used to construct an indwelling blood glucose sensor capable of continuous measurement of glucose levels, although the principle is general and it may be easily seen to extend to the measurement of any analyte of size and charge such that it may be passed through a membrane designed for such purpose.

Example 4

Bioartificial Kidney

Figure 5:
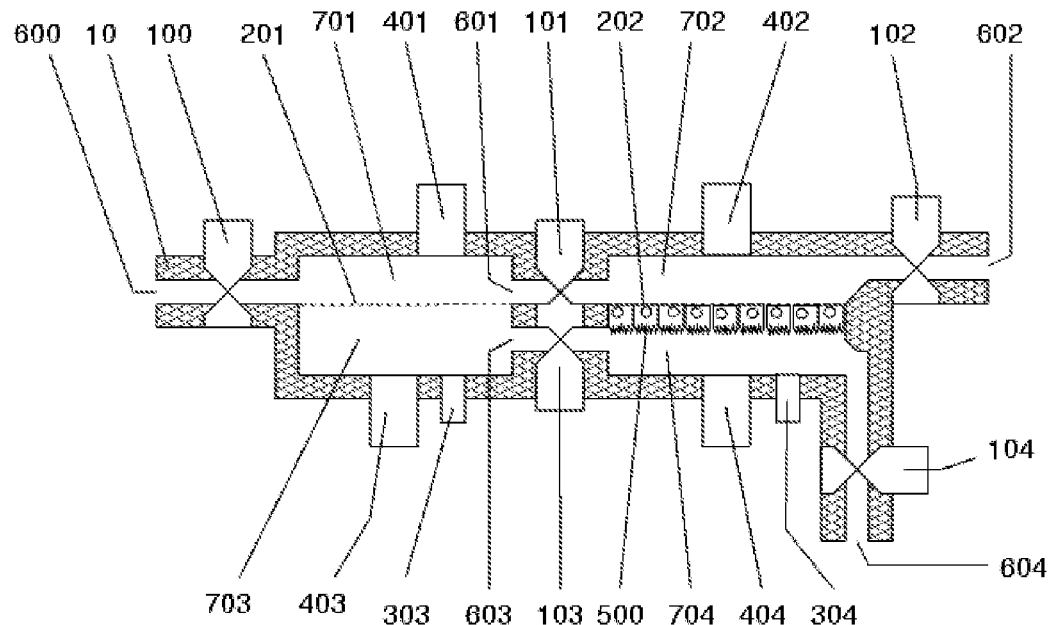
FIG. 5 shows a bioartificial organ in some embodiments of the present invention.

This example demonstrates how nanofabricated nanoporous membranes may be used to form a bioartifical kidney device. A preferred embodiment is shown in FIG. 5. Two membranes 201 and 202 are housed in a housing 10. Blood or other body fluid from a patient is directed via a cannula, vascular graft, vascular anastamosis, or other method into an orifice 600 containing an optional pump or valve 100, which may be peristaltic, rotary, roller, or other, and may be used to regulate a flow of fluid to a chamber in the housing 701, which contains a pressure sensor 401; a membrane 201 composed of a plurality of pores; and an outlet 601 with a flow controlling device such as a pump or valve 101. Said pores may be shaped to optimize hydraulic permeability, and may be all alike or dissimilar. Furthermore, said pores may contain or comprise electrodes, surface treatments, or be coated with chemicals, polymers, proteins, sugars to impart a particular electrostatic charge to the pore or a region around the pore, and impart an electric field within the pore. The outlet 601 and flow controller 101 may be used in conjunction with pressure sensor 401 and pump, valve, or flow controller 100, and external or integrated electronics, telemetry, and information processing to regulate flow of blood or body fluids into and out of chamber 701, and in particular to regulate the hydrostatic pressure in chamber 701. The outlet 601 and flow controller 101 control flow of blood into a second chamber 702, which is equipped with a pressure sensor 402; optionally other sensors incorporating but not limited to optical, conductance, impedance, magnetic resonance, electrochemical, or immunologic principles; and an outlet 602 containing a flow regulating device such as a pump or valve 102. Outlet 602 and its associated flow controller 102 may be used in conjunction with pressure sensor 402 and other pressure sensors and flow controllers and external or integrated electronics, telemetry, and information processing to regulate flow of blood or body fluids into and out of chamber 702, and in particular to regulate the hydrostatic pressure in chamber 702. Blood or body fluids exiting orifice 602 is returned to the patient via a cannula, vascular graft, vascular anastomosis, or other method.

A third chamber 703 is positioned to receive ultrafiltrate generated by hydrostatic pressure or electrosmotic flow of blood or body fluid in chamber 701 passing through the membrane 201, and incorporates a second pressure sensor 403; a sensor or array of sensors 303 incorporating but not limited to optical, conductance, impedance, magnetic resonance, electrochemical, or immunologic principles; and an outlet 603 and flow controller 103. In the example of a bioartificial kidney, it is contemplated that this ultrafiltrate is substantially free of proteins and cellular elements. Flow controller 103 directs ultrafiltrate to a fourth chamber 704, similarly equipped with a pressure sensor 404 and other sensors 304 incorporating but not limited to optical, conductance, impedance, magnetic resonance, electrochemical, or immunologic principles, and an outlet 604 with a flow control mechanism 104. The sensor or array of sensors 304 may be used to monitor the composition of the ultrafiltrate and actuate alarms, valves, or other devices, including but not limited to telemetry and telephony devices, in event that a parameter measured of the ultrafiltrate falls out of a prescribed range.

Chambers 702 and 704 are connected by a second membrane 202 which may be treated, coated, adsorbed, or otherwise modified with cells or tissues. For example, in some embodiments, the cells comprise epithelial, endothelial, fibroblast, or other cells. In some embodiments, the cells are transgenic cells that are engineered to express or not express desired genes (e.g., to modulate the secretion of proteins or other secreted molecules, to express extracellular molecules that bind desired ligands, etc.). In some embodiments, the membrane 202 is also associated with sorbents, enzymes, proteins, channels, porins, or other agents to control and direct the flow of fluids, electrolytes, toxins, peptides, proteins, or other chemicals, through said membrane 202 and into chamber 702 where such fluids, electrolytes, toxins, peptides, proteins, or other chemicals mix with the blood or body fluid that has entered chamber 702 via orifice 601. Blood or body fluid that has been mixed with the cellular and metabolic products of the membrane 202 is then returned to the patient via orifice 602 as described. The ultrafiltrate which has been processed by the second membrane but has not been reabsorbed is carried away from chamber 704 via an outlet 604 and is then carried to a reservoir or to the patient's urinary bladder, an enteric loop, or other suitable disposal route. Through this means, as well as others not specified herein, a patients bloodstream may be filtered and processed to remove solutes, toxins, electrolytes, and water while preserving circulating volume, small peptides, amino acids, and other molecules essential to homeostasis.

A sacrificial oxide technique was used to fabricate arrays of 1 mm×1 mm silicon membranes with 10-100 nm×45 μm slit pores. There were approximately $10^4$ slit pores per array. After etching away the sacrificial oxide, the membranes were epoxied to an acrylic or polycarbonate carrier and inspected via light microscopy for defects. A custom-built apparatus was used to test the membranes. Acrylic was machined to provide two cylindrical half-chambers, each with inlet and outlet Luer fittings. A pressure transducer (Omega PX61) was threaded into a separate port in one chamber. The two halves were bolted together, trapping the membrane and carrier between. Buna-N O-rings provided watertight and gastight seals between the two half-chambers and the membrane carrier. A Luer manifold system allowed regulation of fluid flow into each half chamber. Driving force for gas flow was provided by compressed gas cylinders and for liquid flow by a peristaltic pump. Independent control of flow rate into each chamber and pressure within each chamber was achieved by varying the diameter of tubing draining the chamber. The volumetric flows of gases and liquid were measured by timing positive displacement of a liquid meniscus in calibrated pipettes or syringes.

Nitrogen and carbon dioxide were individually used to flush both sides of the membranes. The outlet of the feed side and the inlet of the permeate side were closed. The outlet on the permeate side was connected to the top of a pipette filled with vacuum oil. The feed side was pressurized at 1.00, 1.25, 1.50, 1.75, and 2.00 psi, and the downward displacement of oil was timed at each pressure. By regulating the height of the meniscus from run to run, the outlet pressure was held to within 2-3 cm oil from experiment to experiment. Tests with dummy membranes without pores and open membranes with macroscopic holes were also conducted to validate the system. The gas flow through the membranes was used initially to confirm that the membrane pores were open and was consistent in performance between and within wafers. Furthermore, carbon dioxide is an ideal wetting agent prior to aqueous experiments, as $CO_2$ bubbles readily dissolve into aqueous solution and allow avoidance of surface tension issues with nitrogen bubbles. Phosphate buffered saline (PBS) was stored in a reservoir and circulated with a peristaltic pump. After membrane flushing with carbon dioxide to exclude air bubbles within the pores, both sides of the membranes were flushed with PBS, and the inlet port of the permeate side sealed. The outlet port was connected to a calibrated syringe barrel, and an oil seal was placed on the syringe barrel. Flow through the feed side of the chamber was adjusted to produce transmembrane pressures of 1.00, 1.25, 1.50, 1.75 and 2.00 psi. Volumetric displacement of the PBS-air meniscus under the oil seal was timed to calculate volume flow. Pressure-flow curves were generated for each pore size and hydraulic permeabilities for PBS were calculated. Measured hydraulic permeabilities correlated well with Navier-Stokes predictions for Hele-Shaw flows (Fissell et al., J. Amer. Soc. Nephrology, vol. 13, pp. 602A, 2002). Also noteworthy were the similarities in hydraulic permeabilities (Kuf) of the silicon nanoporous membranes and commercial polymer dialysis membranes (Fresenius and Baxter). This is particularly interesting considering that the silicon membranes have a porosity that is orders of magnitude smaller than that of polymer membranes.

Silicon chips 1×1 cm square were diced from a 100 mm diameter, 500 μm thick, <100>-oriented n-type single-side polished wafer. Similarly, 1×1 cm square chips of polycrystalline silicon (polysilicon) were diced from a 100 mm diameter, <100>-oriented, n-type single side polished wafer that was oxidized to grow a 1000 Å-thick oxide layer followed by the deposition of a 5 μm thick polysilicon film by low-pressure chemical vapor deposition. Murine collagen IV and fetal calf serum were nonspecifically adsorbed onto steam-autoclaved silicon and polysilicon chips, which were placed in 12 mm-diameter tissue culture wells. Human renal proximal tubule cells (RPTCs) were harvested from transplant discards and grown to fourth passage on 100 mm-diameter tissue culture plates, resuspended, and stained with a fluorescent cell linker (PKH26-GL, Sigma, St. Louis) (Humes et al., Amer. J. Physiology, 271:F42, 1996). Aliquots of $10^5$ cells were layered onto silicon and polysilicon chips with preadsorbed extracellular matrix proteins.

Cell growth was monitored by light microscopy in control wells. When cells reached approximately 75% confluence, 90% confluence, and complete confluence, chips were removed from tissue culture media and fixed in cold 4% paraformaldehyde for 20 minutes and then rinsed with cold phosphate buffered saline and stored in PBS at 0° C. Renal proximal tubule cells were observed to attach to single-crystal silicon and polysilicon chips when pretreated with ECM proteins, and retain surface markers characteristic of renal proximal tubule cells, including tight junction proteins. Specifically, areas of the silicon chips where the membranes were open and porous (M) were compared with areas where the silicon surface was identically textured and prepared, but a monocrystalline silicon backing layer occluded the pores (S). Silicon chips bearing membranes upon which HPTCs had been grown to confluence were incubated with antibodies to two protein markers of differentiation (acetylated tubulin (AT1) and ZO-1). Fluorescently labeled secondary antibodies were then used to examine the cells by immunofluorescence microscopy. A fluorescent marker for cell nuclei (DAPI) was used as a control. Cells attached to S areas and M areas in approximately equal density, and intensity of fluorescence of the DAPI stain did not vary appreciably between S areas and M areas. ZO-1 expression on the surfaces of HPTCs in M areas was increased compared with S areas, although at the time of cell fixation it had not localized to intercellular junctions. Intensity of fluorescence of DAPI was similar between the two areas. Acetylated tubulin is a component of the primary cilium of renal proximal tubule cells. Acetylated tubulin staining in M areas was more intense than in S areas, although DAPI staining remained uniform in intensity over the two areas. These observations show that detailed structuring of surface textures and porosity of silicon nanoporous membranes has direct impact of cellular differentiation.

Example 5

Nanoporous Membranes for Bioartifical Organs

Figure 6:
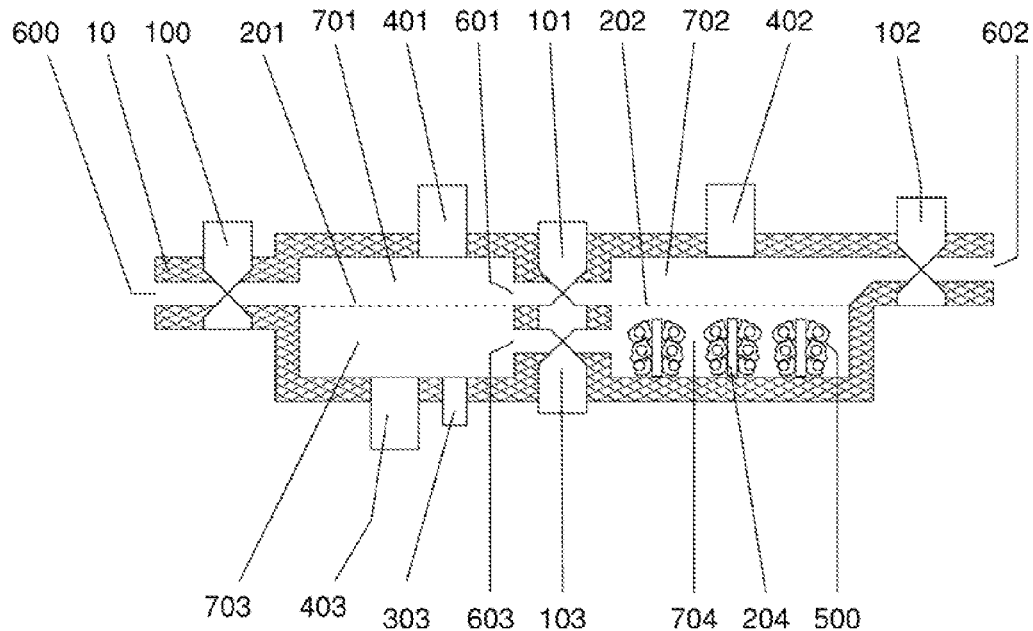
FIG. 6 shows a bioartificial organ in some embodiments of the present invention.

This example demonstrates how nanofabricated nanoporous membranes may be used to form a bioartifical kidney device. A preferred embodiment is shown in FIG. 6. Two membranes 201 and 202 are housed in a housing 10. Blood or other body fluid from a patient is directed via a cannula, vascular graft, vascular anastamosis, or other method into an orifice 600 containing an optional pump or valve 100, which may be peristaltic, rotary, roller, or other, and may be used to regulate a flow of fluid to a chamber in the housing 701, which contains a pressure sensor 401; a membrane 201 composed of a plurality of pores; and an outlet 601 with a flow controlling device such as a pump or valve 101. Said pores may be shaped to optimize hydraulic permeability, and may be all alike or dissimilar. Furthermore, said pores may contain or comprise electrodes, surface treatments, or be coated with chemicals, polymers, proteins, sugars to impart a particular electrostatic charge to the pore or a region around the pore, and impart an electric field within the pore. The outlet 601 and flow controller 101 may be used in conjunction with pressure sensor 401 and pump, valve, or flow controller 100, and external or integrated electronics, telemetry, and information processing to regulate flow of blood or body fluids into and out of chamber 701, and in particular to regulate the hydrostatic pressure in chamber 701. The outlet 601 and flow controller 101 control flow of blood into a second chamber 702, which is equipped with a pressure sensor 402; optionally other sensors incorporating but not limited to optical, conductance, impedance, magnetic resonance, electrochemical, or immunologic principles; and an outlet 602 containing a flow regulating device such as a pump or valve 102. Outlet 602 and its associated flow controller 102 may be used in conjunction with pressure sensor 402 and other pressure sensors and flow controllers and external or integrated electronics, telemetry, and information processing to regulate flow of blood or body fluids into and out of chamber 702, and in particular to regulate the hydrostatic pressure in chamber 702. Blood or body fluids exiting orifice 602 is returned to the patient via a cannula, vascular graft, vascular anastamosis, or other method.

A third chamber 703 is positioned to receive ultrafiltrate generated by hydrostatic pressure or electrosmotic flow of blood or body fluid in chamber 701 passing through the membrane 201, and incorporates a second pressure sensor 403; a sensor or array of sensors 303 incorporating but not limited to optical, conductance, impedance, magnetic resonance, electrochemical, or immunologic principles; and an outlet 603 and flow controller 103. In the example of a bioartificial kidney, it is contemplated that this ultrafiltrate is substantially free of proteins and cellular elements. Flow controller 103 directs ultrafiltrate to a fourth chamber 704, optionally equipped with a pressure sensor and other sensors not shown incorporating but not limited to optical, conductance, impedance, magnetic resonance, electrochemical, or immunologic principles. In some embodiments, chamber 704 is fitted with nanofabricated or other assemblies 204, which may be treated, coated, adsorbed, or otherwise modified with cells or tissues 500. In some embodiments, these cells may be pancreatic islet cells. In some embodiments these may be hepatocytes. In other embodiments these may be transgenically modified cells, prokaryotic or eukaryotic cells, bone marrow cells, xenotransplanted cells, allografted cells, or stem cells of embryonic or adult origin of human or other species. These examples shall not be construed as limiting the type, variety and mixtures of cells to be employed. In this example, cells 500 are permitted to be bathed by the ultrafiltrate of blood generated by membrane 201 and delivered to them from chamber 703 via orifice 603. In some embodiments, said ultrafiltrate is free of immunoglobulins, complement components of blood, chemotherapeutic agents, or other entities in the blood harmful to cells 500. Said cells 500 may metabolize toxins in the ultrafiltrate, in the example in which they are hepatocytes, or may sense the concentration of some entity in the ultrafiltrate, such as glucose, and respond by secreting a hormone or other molecule, such as insulin. In another embodiment, cells 500 may be renal cells that secrete erythropoetin in response to oxygen tension in the ultrafiltrate. Chambers 702 and 704 are connected by a second membrane 202 that may be treated, coated, adsorbed, or otherwise modified with cells or tissues. In some embodiments, the membrane 202 is also associated with sorbents, enzymes, proteins, channels, porins, or other agents to control and direct the flow of fluids, electrolytes, toxins, peptides, proteins, or other chemicals, through said membrane 202 and into chamber 702 where such fluids, electrolytes, toxins, peptides, proteins, or other chemicals mix with the blood or body fluid that has entered chamber 702 via orifice 601. In some embodiments, the porous structure of membrane 202 is designed to prevent passage of a specified protein, peptide, sugar, lipid, bacterium, or other entity into chamber 702. Blood or body fluid that has been mixed with the cellular and metabolic products of the membrane 202 is then returned to the patient via orifice 602 as described. Through this means, as well as others not specified herein, a patient may receive a dose of cells of arbitrary type while such cells are protected from the immune effectors in the blood, while receiving convective transport of nutrients and oxygen from the blood, and the biological products of such cells may re-enter the patient's bloodstream in a controlled fashion.

Example 6

This example describes the fabrication of nanopore membranes employing certain embodiments of the invention. Nanopore membranes with monodisperse pore size distribution have been prototyped from silicon substrates by a process based on MEMS technology (see, e.g., Lopez, C. A., et al., Biomaterials, 2006. 27(16): p. 3075; Fissell, W. H., et al., Blood Purif, 2007. 25(1): p. 12). The process used the growth of a thin sacrificial $SiO_2$ (oxide) layer to define the critical submicron pore size of the filter. The oxide was etched away in the final step of the fabrication process to leave behind open pores in the form of, for example, parallel-plate nanochannels. Thermal oxidation of silicon substrates provided oxides down to 5 nm in thickness with <1% variation across the wafer.

Figure 10:
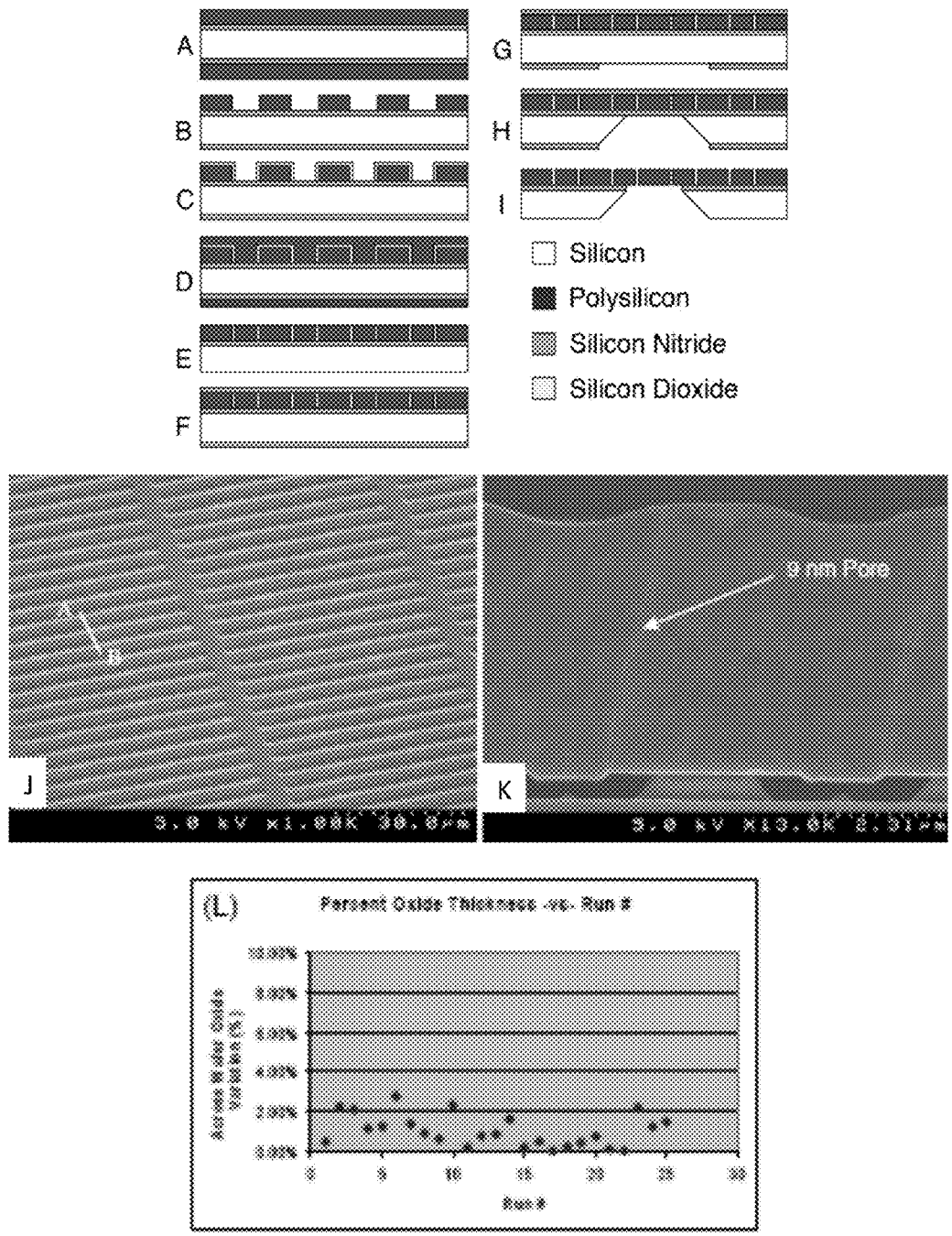
FIG. 10 shows a nanoporous membrane of an embodiment of the present invention. Fabrication of nanoporous membranes (A-I) depicted via wafer cross-sections (not to scale). The critical pore dimension (SiO2 thickness in C) can be controlled between 5-50 nm just by changing oxidation parameters. SEM images of nanoporous membrane showing top view (J) and cross-section (K). Scatter plot (L) shows across-wafer oxide thickness uniformity variation of <1% (maximum 3%) from 25 different oxidation runs.

The starting substrate was a 400 μm-thick, 100 mm-diameter, double side polished<100>-oriented silicon wafer that was obtained from a commercial vendor of semiconductor substrates. The wafer was coated with a 500 nm-thick layer of low-stress silicon nitride (LSN) followed by a 5 μm-thick film of polycrystalline silicon (polysilicon) (FIG. 10(a)). The polysilicon layer was patterned by photolithography and reactive ion etching (RIE) to create 50 μm-long spaces and lines that were 2-3 μm wide (FIG. 10(b)). Thermal oxidation of the patterned polysilicon was performed to grow a thin conformal SiO2 film that defined the pore size in the nanoporous membrane (FIG. 10(c)). The thickness of this conformal SiO2 film can be readily varied between 5-100 nm by adjusting oxidation parameters such as time and temperature. After deposition of another 4 μm-thick polysilicon film, chemical-mechanical polishing was performed to expose the nanopore regions on the frontside (FIG. 10(e)). LSN was deposited on both front and back sides of the wafer (FIG. 10(f)). The LSN on the wafer backside was patterned to define an etch mask (FIG. 10(g)). The wafer was subsequently etched in KOH to create suspended membranes (FIG. 10(h)). Finally, the masking LSN and $SiO_2$ films were etched in concentrated hydrofluoric acid to produce nanoporous membranes with 40 μm-long slit pores with nanoscale pore width (FIG. 10(i,j,k)).

Membranes with critical pore widths of 5-100 nm have been routinely fabricated with <1% mean pore size variation across a 100 mm-diameter wafer (FIG. 10(l)). For experiments, the wafer was sized into 1×1 cm chips bearing arrays of 1×1 mm nanoporous membranes. Each membrane was ~4 μm thick and contained ~104 slit pores, which translated to overall porosity of ~1%. Recent advances in nanoimprint lithography technology make it feasible to generate lines and space patterns down to <50 nm (see, e.g., Guo, L. J., Journal of Physics D: Applied Physics, 2004. 37: p. R123; Tallal, J., et al., Microelectronic Engineering, 2005. 78-79: p. 676). In some embodiments, this capability permits closer pore packing, and increase membrane porosity from ~1% (2 μm pore separation) to >20% (<100 nm pore separation). In some embodiments, uniform oxide films down are grown to 2 nm on singlecrystal silicon (see, e.g., Bidaud, M., et al., Journal of Non-Crystalline Solids, 2001. 280(1-3): p. 32).

Example 7

This example describes the biocompatibility of MEMS materials. Silicon (Si), silicon dioxide ($SiO_2$), and silicon carbide (SiC) were examined using a battery of standardized in vitro test protocols based on the International Standards Organization (ISO) Biocompatibility Guideline (ISO 10933); incorporated herein by reference in its entirety. The MEM Elution Test was used to evaluate the materials for potential cytotoxic effects with black rubber and polypropylene as the positive and negative controls, respectively. Extracts of the test materials were added to cell culture plates seeded with L-929 mouse fibroblast or WI-38 human embryonic lung cells and incubated at 37° C. with 5% $CO_2$ for 48 hours. Cell culture plates were then examined microscopically (100×) to determine any change in cell morphology and lysis, monolayer confluency, and color as an indicator of resulting pH. Results were scored on a scale of 0-4, where 0 represented the best case—no adverse reaction whatsoever—and 4 represented the worst case—complete cell lysis. A score of 2 or below was considered acceptable for many implantable applications.

Negative and positive controls exhibited grades of 0 and 1, respectively. Si, $SiO_2$, and SiC exhibited a grade of 0 meaning that such materials do not exhibit any cytotoxicity, and could be exposed to the in vivo biological environment. Similar results were obtained for in vivo irritation tests from implantation into rabbit musculature.

Si and $SiO_2$ were subsequently evaluated for hemocompatibility to ascertain whether they would adversely induce hemolysis, osmotic fragility, or coagulation. The hemolysis test is a standard method to determine the amount of blood cell lysis caused by a material sample. Extract samples were incubated with citrated human blood cells from healthy donors in 0.9% saline for 1 hour at 37° C. Afterwards intact red blood cells were removed and the optical density of the supernatant fluid was analyzed using a spectrophotometer set at 540 nm. The optical density readings of the sample were normalized to those from the positive and negative controls to determine net hemolysis due to the material being tested. The results showed that Si and $SiO_2$ did not exhibit hemolysis. The osmotic fragility test is an extension of the standard hemolysis test and was used to determine the relative increase in hemolysis with decreasing osmotic pressure caused by a material sample. The results showed that none of the MEMS material samples induced osmotic fragility.

The effect of Si and $SiO_2$ on blood coagulation was examined using the partial thromboplastin test (PTT) and prothrombin time (PT) test, which are general screening tests for the detection of abnormalities in the intrinsic and extrinsic pathways, respectively. In the PTT test, the sample extract was incubated with PTT reagent for 3 minutes at 22° C., and afterwards clotting time was determined after addition of calcium chloride reagent. In the PT test, the extract was added to calcium chloride and thromboplastin reagents and the resulting clotting time is determined. Clotting times of the material samples were compared to corresponding times from polypropylene samples, which act as negative control. The results from the PTT and PT tests showed that $SiO_2$ exhibited a slight variation (p<0.05) in clotting time, while Si exhibited clotting behavior that was consistent with the negative control.

In summary, results of the biocompatibility tests confirm that the primary constituent materials of the nanoporous membranes—Si and $SiO_2$; the latter forms on exposed Si surfaces—are suitable for an implantable hemofilter and tubule bioreactor.

Example 8

This example describes surface modification of the nanopore membranes. To explore the functionality of solution phase coupled PEG to the previously mentioned nanoporous membranes the method employed by Larson et al. was utilized (see, e.g., Papra A, et al., Langmuir 17:1457-1460 (2001); incorporated herein by reference in its entirety). This technique uses a single-step mechanism which covalently couples silicon surface silanol groups (Si—OH) to a PEG polymer through a trimethoxysilane group forming a Si—O—Si-PEG sequence by a methanol dehydration reaction. This method is appealing due to the ease of application and availability of commercial materials that can be used as received. It is a one step procedure as opposed to other processes such as CVD, or solution phase coupling that use a bridge molecule to form a covalent bond. For this reason, this deposition technique with slight modifications was utilized. The modifications included omitting all sonication steps and continuing the PEG deposition for 12 hours.

Figure 8:
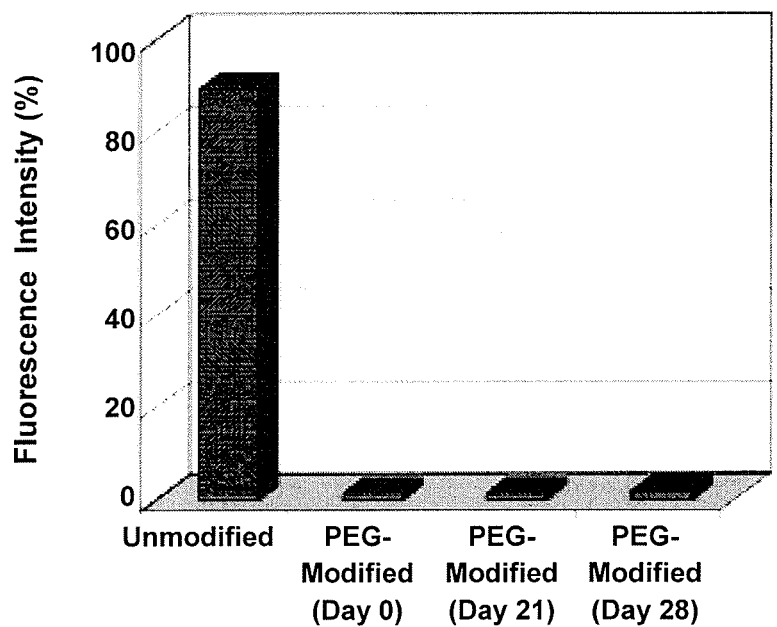
FIG. 8, taken from Sharma et al., 2004 Langmuir 20(2), shows the resistance of PEG coatings to protein fouling. LEFT—Fluorescence intensity for unmodified and PEG-modified surfaces over a period of 4 weeks. Samples were incubated in FITC-BSA (0.5 mg/mL in PBS, pH 7.4, 37° C.) for 1 hour. CENTER—Adhesion of fibroblasts to silicon and PEG-modified silicon substrates: (A) control (silicon); (B) PEG-modified silicon (O week incubation period); (C) PEG-modified silicon (after 4-week incubation period). RIGHT—Variation in protein adsorbed on PEG thin films of various grafting densities (ellipsomeric measurements0. Solid lines show the fit for the expotential decay model ($y=y_o+ae^{-bx}$).
Figure 8:
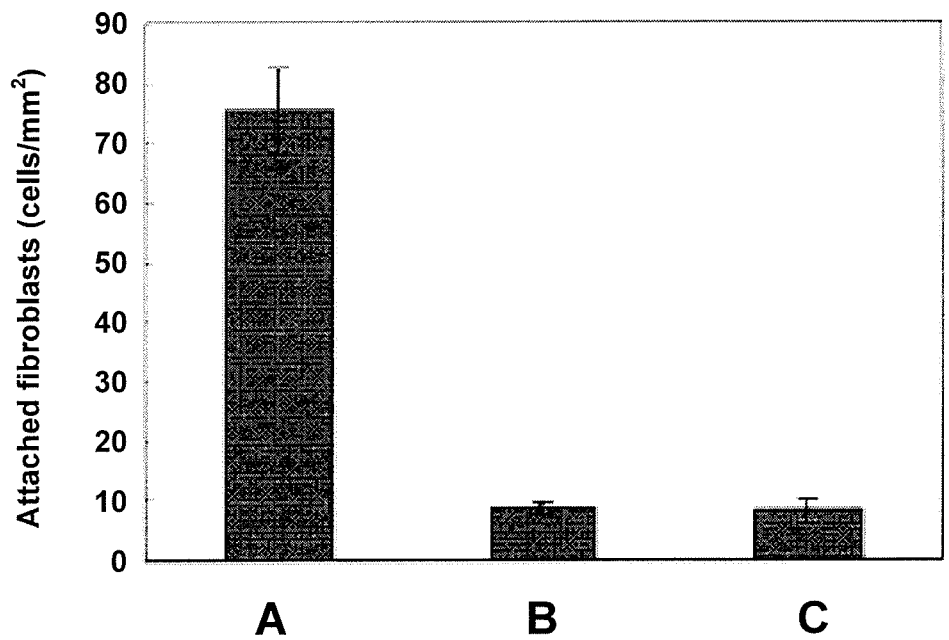
Figure 8:
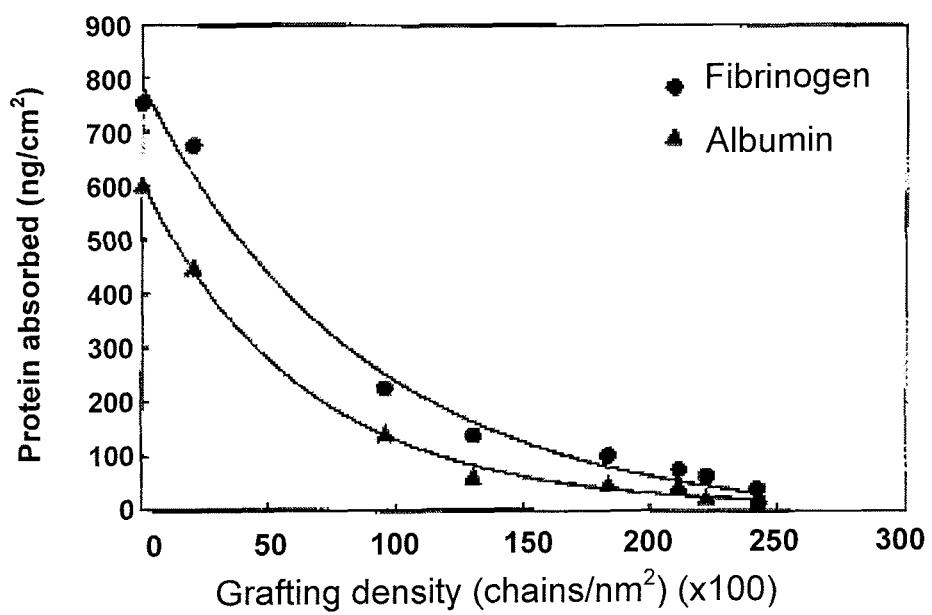

Resistance of the PEG coatings to protein fouling was examined (taken from Sharma et al., 2004 Langmuir 20(2)) with albumin (see, FIG. 8, left) and fibrinogen. Both protein deposition and fibroblast attachment (see, FIG. 8, center) were reduced by 90% on PEG modified substrates relative to uncoated controls. The optimal grafting surface density was determined to be 20000-25000 PEG molecules per $nm^2$ (see, FIG. 8, right). Contact angle measurements confirmed that bare silicon is more hydrophilic (~10°) compared to PEG modified surfaces (~350), which is still less hydrophobic than silanized silicon (~80°). Also, the contact angle did not depend on the concentration of EtO, suggesting that the surface is uniformly coated with PEG. Stability of PEG films was confirmed over a 4-week period. The modified surfaces (CVD PEG coatings) were kept at 25° C. (room temperature) to study their dry stability and at 37° C. in PBS to study their aqueous stability. The composition of the film was determined after 4 weeks. Analysis of the surfaces by x-ray photoelectron spectroscopy (XPS) indicated that the PEG films remained extremely stable in the dry environments, while in PBS solution, the carbon content of the PEG film was reduced by 7%. Contact angles measured after 4 weeks in dry and aqueous conditions was 38±3°, indicating that the PEG modified surface was also stable in terms of hydrophilicity.

Figure 9:
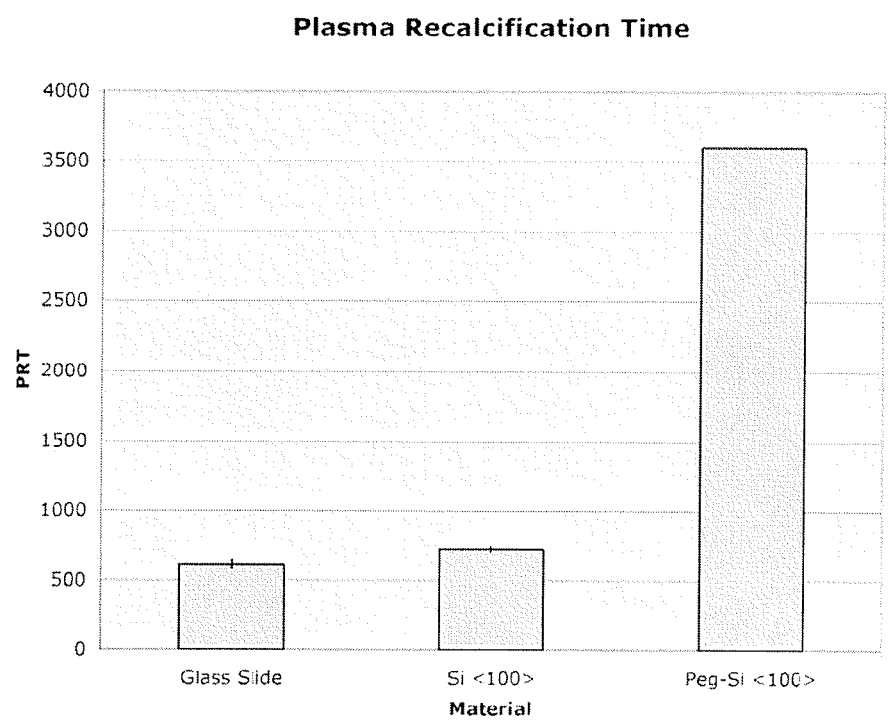
FIG. 9 shows silicon membranes coated with PEG have increased plasma recalcification time in comparison to silicon membranes lacking PEG coating and glass slides.

FIG. 9 shows silicon membranes coated with PEG have increased plasma recalcification time in comparison to silicon membranes lacking PEG coating and glass slides.

Example 9

This example describes hydraulic permeability testing for the nanopore membranes. Nanoporous membrane chips (1×1 cm) were epoxied to an acrylic or polycarbonate carrier and mounted in a custom-built apparatus to test the membranes for fluid transport characteristics (see, FIG. 10). Acrylic was machined to provide two cylindrical half-chambers, each with inlet and outlet Luer fittings. A pressure transducer (Omega PX61) was threaded into a separate port in one chamber. The two halves were bolted together, trapping the membrane and carrier between. Buna-N O-rings provided watertight and gastight seals between the two half-chambers and the membrane carrier.

A Luer manifold system allowed regulation of fluid flow into each half chamber. Driving force for gas flow was provided by compressed gas cylinders and for liquid flow by a peristaltic pump. Independent control of flow rate into each chamber and pressure within each chamber were achieved by varying the diameter of tubing draining the chamber. The volumetric flows of gases and liquid were measured by timing positive displacement of a liquid meniscus in calibrated pipets or syringes.

Phosphate-buffered saline (PBS) was stored in a reservoir and circulated with a peristaltic pump. After membrane flushing with carbon dioxide to prime the pores, both sides of the membranes were flushed with PBS, and the inlet port of the permeate side sealed. The outlet port was connected to a calibrated syringe barrel, and an oil seal was placed on the syringe barrel. Flow through the feed side of the chamber was adjusted to produce transmembrane pressures of 1.00, 1.25, 1.50, 1.75 and 2.00 psi.

Volumetric displacement of the PBS-air meniscus under the oil seal was timed to calculate volume flow. Pressure-flow curves were created for each pore size, and hydraulic permeabilities for PBS were calculated.

Example 10

This example describes membrane permselectivity testing with the nanopore membranes. Membrane arrays were examined under differential interference contrast light microscopy for defects. Defective membranes within an array were sealed with medical-grade epoxy (Loctite HM-100) and the array mounted in a custom-made Ussing chamber. Hydraulic permeability to $CO_2$ and phosphate-buffered saline (PBS) of each membrane was compared to historical controls ($CO_2$) and first-principles Navier-Stokes predictions (PBS). Membranes with measured hydraulic permeability to PBS greater than 2× predicted were rejected. The retentate side of the membrane was continuously perfused at a flow rate of 1 ml/min from a 100 ml reservoir of retentate, and the permeate side of the membrane was wetted with 60 uL of PBS. Compressed air was used to generate transmembrane pressures of 0, 1 or 2 psi as monitored by a pressure transducer within the Ussing chamber (Entran, Inc). The membrane was perfused for 200 hours with a solution of 4 mg/ml bovine serum albumin (Sigma, St. Louis) in PBS. The ultrafiltration volume was monitored either in a calibrated syringe barrel (Hamilton) capped with parafilm, or in a length of microbore tubing the tip of which was immersed in saline. Membranes were perfused with polydisperse FITC-labelled Ficoll 70 (50 ug/ml) prepared. Permeate was collected at timed intervals at zero membrane flux (diffusion-only data) and at 1 and 2 psi driving pressure, corresponding to membrane fluxes of approximately $10^{-8}$ m/s. Feed and permeate samples were analyzed by gel permeation chromatography with a Waters Ultrahydrogel 500 column on a Waters 600E system using a Waters 474 fluorescence detector. Size calibration of the column was performed with narrow-dispersion Ficoll samples of known size. Leaks were excluded by perfusing the membrane with 200 nm fluorescent beads, and examining the perfusate under a fluorescent microscope.

A hollow-fiber dialyser (F200, Fresenius) was opened and individual hollow fibers potted in Luer fittings with medical-grade epoxy (Loctite HM-100). Sample hollow fibers were perfused with Ficoll 70 by a circuit similar to that described above, and transmembrane pressure was set at 2 psi. Ultrafiltrate samples were collected by gravity.

Figure 7:
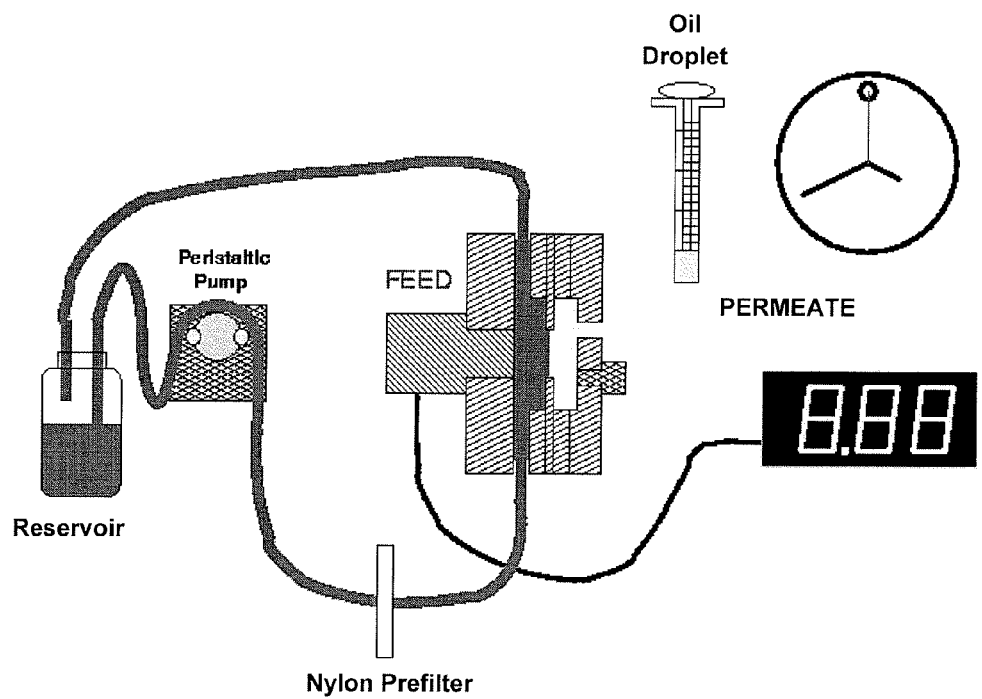
FIG. 7 shows a custom-built test apparatus for pressure-driven flow characterization experiments.

Sieving coefficients (fractional transmission) of three candidate proteins (ovalbumin, 45 kD, bovine serum albumin, 66 kD, and transferrin, 76 kD) were individually tested with a 30 nm-wide slit pore membrane mounted in the custom-built apparatus (see, FIG. 7). Solutions of each protein at 1 mg/ml concentration in pH 7.4 PBS without calcium were prepared and protein concentration confirmed by Bradford assay. Next, a feed solution of bovine serum albumin was circulated on the feed side of the membrane, with continuous tangential flow at 1-2 ml/min across the face of the membrane. Transmembrane pressures were adjusted to produce steady generation of permeate. After 100 μL of permeate was collected, it was removed for analysis along with a simultaneous aliquot of feed solution.

Figure 11A:
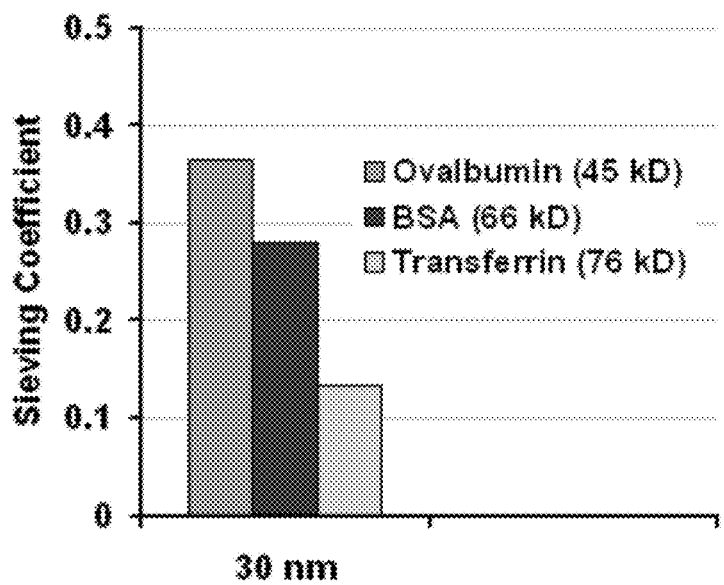
FIG. 11A shows sieving coefficients of candidate proteins through nanoporous membrane (30 nm-wide slit pores) showing some permselectivity.
Figure 11B:
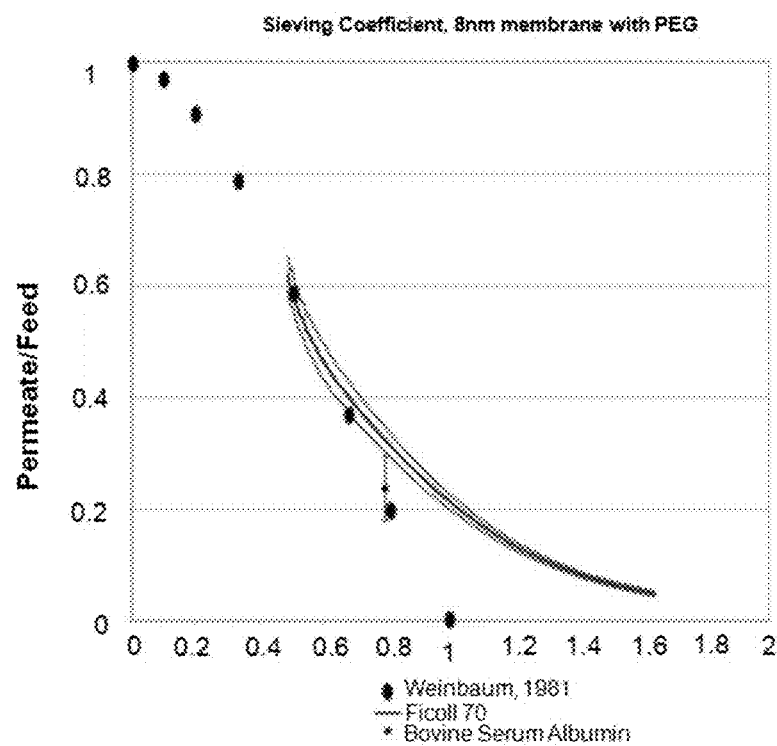
FIG. 11B shows sieving coefficients (σ) of Ficoll 70 and BSA compared to theoretical prediction based on steric hindrance. λ refers to the ratio of molecule diameter to nanopore size. σBSA=0.24 for an 8 nm pore.
Figure 12:
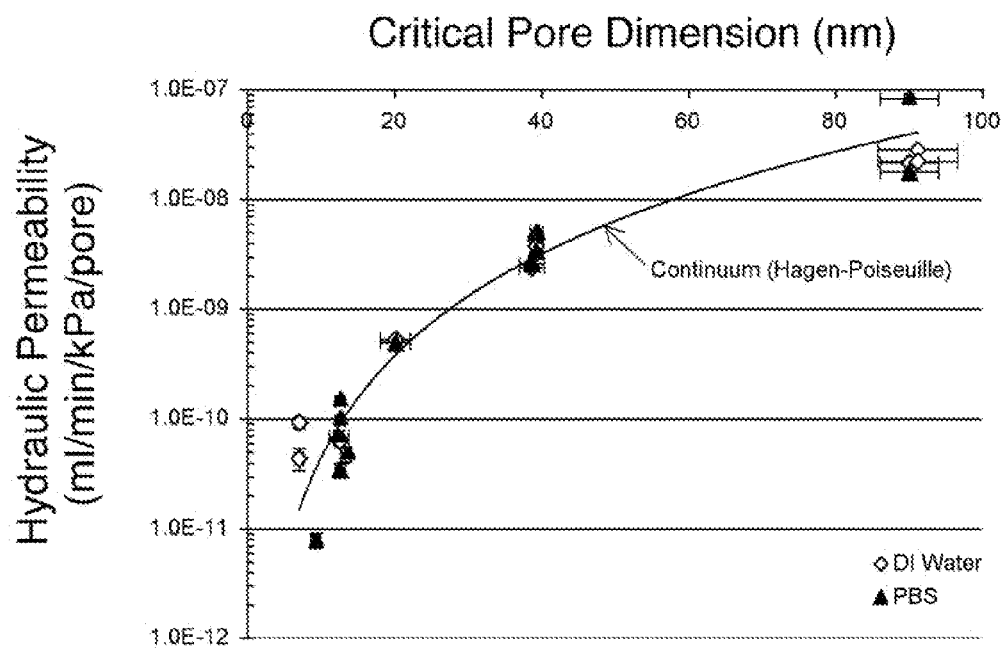
FIG. 12 shows the hydraulic permeability of a nanoporous membrane of the present invention.
Figure 13:
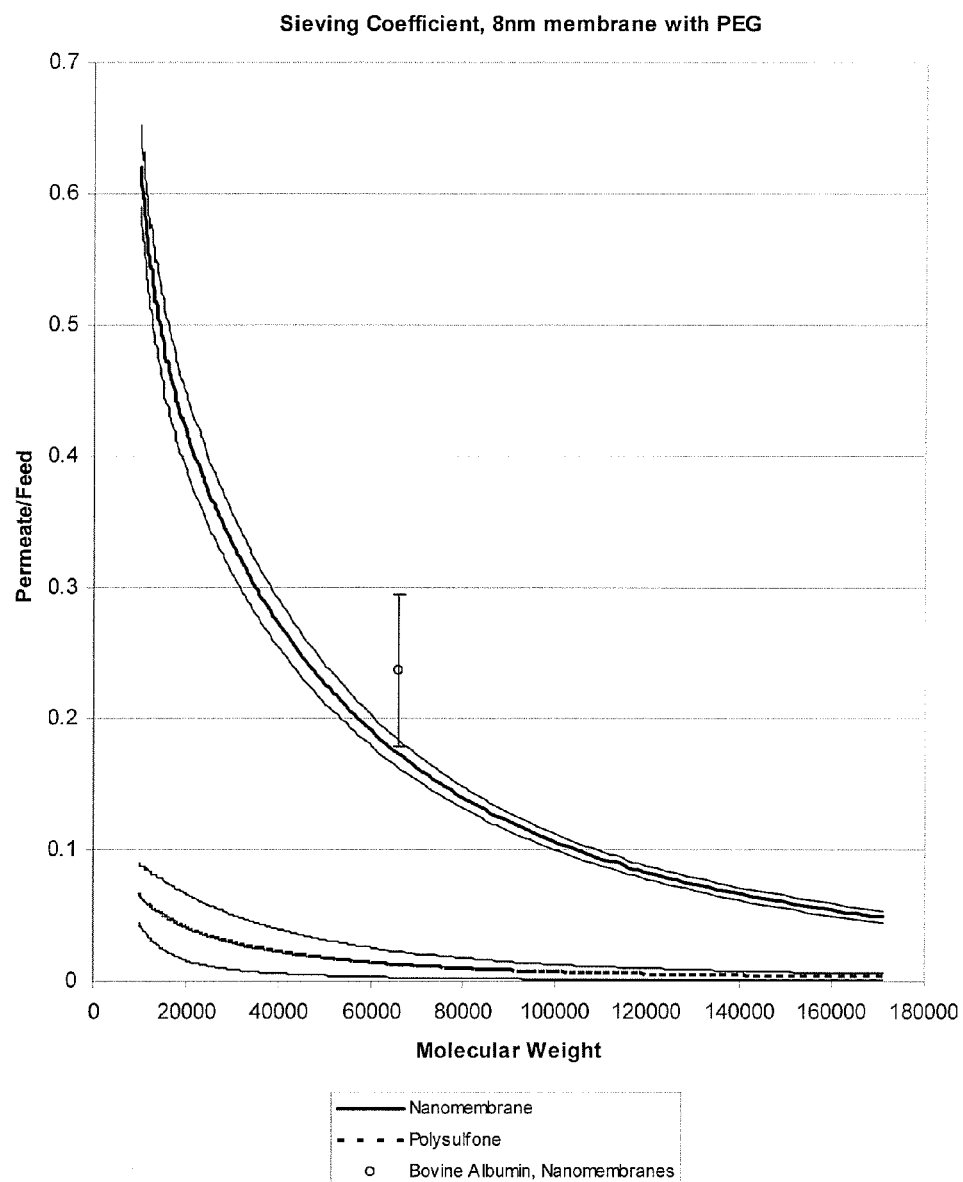
FIG. 13 shows the permselectivity of a nanoporous membrane of the present invention.

The experiment was similarly repeated for ovalbumin and transferrin. Protein concentrations in feed and permeate were measured. Dead-space volume in the permeate chamber was measured by weighing the permeate volume, and protein concentration in permeate was normalized to account for this dilution. Significant hindered transport was observed for all proteins in a size-dependent fashion (see, FIG. 11A) despite the fact that the membrane critical pore size was 3-5× than the molecular diameter of the proteins. Solute transport of bovine serum albumin (BSA, Mw=66 kD) and Ficoll 70 (Mw=10-250 kD) was measured using a PEG-modified membrane with 8 nm-wide pores mounted in the Fluid Flow Testing Station. A continuous flow of 50 μg/ml of FITC-labeled Ficoll 70 in PBS was established across the FEED side, and pressurized with compressed air to 2.0 psi to collect 80-110 μL of ultrafiltrate in the PERMEATE chamber. Afterwards, FEED and PERMEATE aliquot sample chromatograms were analyzed by gel permeation chromatography with a Waters Ultrahydrogel GPC column on a 600E system. An identical procedure was followed with BSA, except that the FEED and PERMEATE protein concentrations were measured by Bradford assay. Sieving coefficients, σ, were calculated as the ratio of PERMEATE/FEED concentration and compared to λ, which is the ratio of the molecular Stokes-Einstein diameter to nanopore size. The silicon nanoporous membrane displayed size-dependent rejection of solutes as predicted by a steric hindrance model for rigid spheres (FIG. 11B). Specifically, BSA exhibited a sieving coefficient of 0.24, which is close to the predicted value (see, e.g., Weinbaum, S., Lect. Math Life Sci., 1981. 14(119)). For Ficoll 70, transport was observed in excess of predictions for λ>0.8, as has been reported previously (see, e.g., Rippe, C., et al., Kidney Int, 2006. 69(8): p. 1326; Venturoli, D. and B. Rippe, Am J Physiol Renal Physiol, 2005. 288(4): p. F605). The permselectivity data indicates, for example, that the nanopores are very discriminating based on molecular weight/size of the protein. In additional experiments, prototype silicon nanoporous membranes were manufactured with highly uniform smooth walled pores (see, FIG. 10). Gas transport of carbon dioxide, nitrogen, and argon were consistent with transition-regime and Knudsen flow. Membrane hydraulic permeabilities for PBS closely matched first-principles predictions (see, FIG. 12). Hydraulic permeability of an array of six 1 mm² membranes was completely unchanged by extended perfusion with bovine serum albumin (1.0 uL/min/6 mm² at 2.0 PSI before and after BSA). Serial dilutions of retentate and permeate revealed that fluorescent latex beads were observable at $10^{-5}$ to $10^{-6}$ dilution of the retentate but were not observed in the permeate at any dilution. Prototype membranes displayed size-dependent rejection of Ficolls (see, FIG. 13). The molecular weight cutoff of the PEG-modified silicon membrane, as estimated by the molecular weight at which the rejection coefficient is half-maximal, was around 18 kD, compared with less than 10 kD for the polysulfone hollow-fiber dialyser.

Example 11

This example describes the growth of renal tubule cells on nanoporous membranes. Central to the goal of reducing need for replacement fluid is the use of a cell bioreactor to reabsorb salt and water from the ultrafiltrate stream while maintaining a barrier to reabsorption of uremic toxins. Metabolic activity of renal epithelial cells are clinically important in stress states such as septic shock and multisystem organ failure. The renal epithelial cells are typically derived from the cortex of donor kidneys that proved unsuitable for transplant. Cells were seeded into the lumens of conventional polysulfone hollow-fiber dialyzer cartridges and grown to confluence before deployment in the extracorporeal circuit. The polymer surface of the hollow fibers was typically pretreated with Pronectin-L or murine collagen to enhance cell attachment. Early single hollow-fiber experiments demonstrated that solute transport by the cultured renal cortical epithelial cells was an active process, as blocking Na—K-ATPase with oubain, and blocking sodium-dependent glucose transport with phlorizin altered apical-to-basal sodium and glucose concentrations.

Function of a miniaturized implantable device requires a miniaturized bioreactor, which, in turn, is affected by epithelial cell attachment, maintenance of differentiated phenotype, and epithelial tight junction integrity. The suitability of silicon nanoporous membranes as scaffolds for tubule cell bioreactors has been demonstrated. Membranes with 40 nm-wide slit pores were bathed in 30% hydrogen peroxide overnight to improve surface wetting, followed by rinsing with phosphate buffered saline and adsorption of murine collagen IV at 5 μg/cm². Human cortical tubule cells were seeded at 5×10⁵ cells/cm² on nanoporous membranes as well as control polyester cell cultures inserts (Corning Transwell, 0.4 μm pore size) and grown to confluence in hormonally defined media. Transepithelial resistance was measured at intervals across nanoporous membranes and polyester membranes using a standard instrument (EVOMX, World Precision Instruments). Cells appeared confluent after about six days, and the cells were fixed with 4% cold paraformaldehyde after a total of 14d of growth. The cells were stained by indirect immunofluorescence for a tight junction protein, ZO-1, a ciliary protein, acetylated tubulin, and a brush border enzyme, γ-glutamyl transferase, as well as a nuclear stain, 4',6-Diamidino-2-phenylindole (DAPI). Cells grown on silicon nanoporous membranes and on polyester controls showed similarly intense staining for all three proteins, suggesting that the epithelial cells were able to achieve differentiated phenotype similarly on standard tissue culture substrates and on the silicon nanoporous membranes (see, FIG. 14, left). Transepithelial resistance was also highly similar between the two substrates, suggesting the formation of functional tight junctions (FIG. 14, right). These results show, for example, that nanoporous silicon membranes are viable as a scaffold for the cell bioreactor in a miniaturized implantable RAD.

Example 12

This example describes various alternative pore pattern designs and membrane fabrication techniques.

In some embodiments, the present invention provides a target hemofiltration rate of 30 ml/min through arrays of sub-50 nm pores with a transmembrane pressure of 30 mmHg. These embodiments employ will highly porous, yet mechanically robust, membranes. Preferably, the designs are configured to handle filtration, while exhibiting burst strengths of at least 300 mmHg.

Reliability analyses were performed on silicon nanoporous membranes of identical overall size, but several pore arrangements derived from the current design (pore spacing of ~2.5 µm). Stress fields on the membranes under 5 psi (~260 mmHg) transmembrane pressure were examined using finite element methods, and subsequently, reliability analyses were conducted for each stress field using representative Weibull material parameters (see, e.g., Jadaan, et al., Strength and Weibull characterization of polysilicon membranes for MEMS applications. Proceedings of the 30th International Conference & Exposition on Advanced Ceramics & Composites, Cocoa Beach, Fla., 2006). These reliability analyses allowed for comparison of various nanopore arrangements relative to each other.

Table 1 depicts the stress fields and fracture probability of three membrane designs. Design #A shows a baseline solid membrane without any pores, while Design #B presents a membrane design having 2.9% porosity wherein the pores are distributed all over the membrane including the edge and center regions. The corresponding fracture probabilities (~0% for Design #A and 55% for Design #B) indicate that current membrane designs are fragile and fracture slightly above 3 psi, while the solid membranes survive 100 psi transmembrane pressures. In contrast, pore distribution in Design #C has been optimized to avoid membrane edges and the center region, which results in a very low fracture probability (~0%).

The present invention provides a variety of different nanopore arrangement. In some embodiments, pore patterns are provided on membranes in a rectangular configuration (e.g., at least 2:1) rather than a square (1:1 aspect ratio) to mitigate stress levels in the long direction. It is contemplated that these modifications result in a probability of failure that will be <1%. Hydraulic permeability of the membrane can be increased in two ways: (a) porosity can be increased to ~20% by decreasing the pore spacing from 2000 nm to 50 nm; and (b) channel conductance can be increased by decreasing membrane thickness ~4000 nm to 500 nm.

Figure 15:
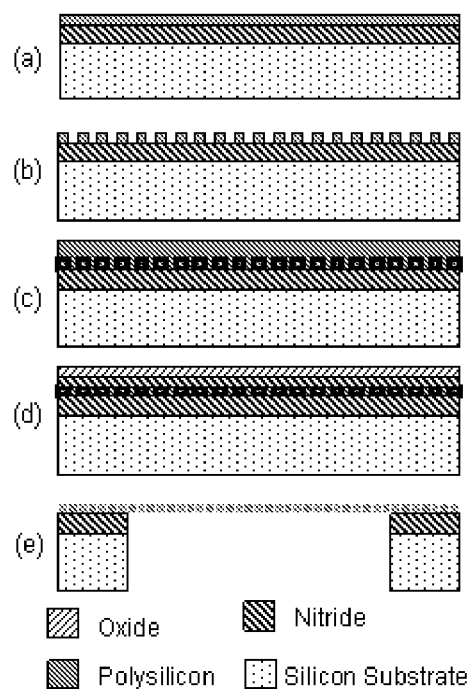
FIG. 15 shows an exemplary membrane manufacture method in some embodiments of the present invention.

In some embodiments, the design for the hemofilter is a 1 micrometer-thick membrane with arrays of 10-50 nm-wide slit pores with 50 nm separation. This membrane geometry and nanopore arrangement is contemplated to achieve 30 ml/min filtration rate with 30 mmHg of transmembrane pressure within an overall membrane area of 0.1 m². In some embodiments, a fabrication approach shown in FIG. 15 is used. FIG. 15 shows the process via cross-sectional fabrication sequence: (a) process begins with deposition of a 1.0 µm low-stress nitride layer and a 1.0 µm polysilicon layer; (b) polysilicon layer is pattered using nanoimprint lithography and RIE; (c) oxidation grows sacrificial oxide layer on the polysilicon; RIE is used to remove oxide on top of polysilicon, and a 0.5 µm-thick polysilicon layer is deposited; (d) polysilicon is polished back on front side and a protective layer of nitride and oxide is deposited on top; (e) cavities are etched from the backside and the pores are opened via a hydrofluoric acid etch. The nanopore arrangement can be of any type described herein. Preferably, the design decreases the pore spacing to as low as 50 nm by nanoimprint lithography (IMPRIO System) and RIE of the polysilicon. In some embodiments, the patterned wafers are then thermally oxidized to grow a 10-50 nm-thick sacrificial oxide layer. The exact thickness of the oxide layer will depend on the pore spacing.

In some embodiments, the fabrication protocols combine nanoimprint lithography, silicon-on-insulator (SOI) technology, and silicon wafer bonding to produce robust nanoporous membranes supported by crossbars. In such embodiments, the pore size is not defined by oxidation, but by a nanoimprint lithography and RIE step. Furthermore, the membranes are constructed from one layer of single crystal silicon, thereby eliminating residual stresses associated with polysilicon.

Figure 16:
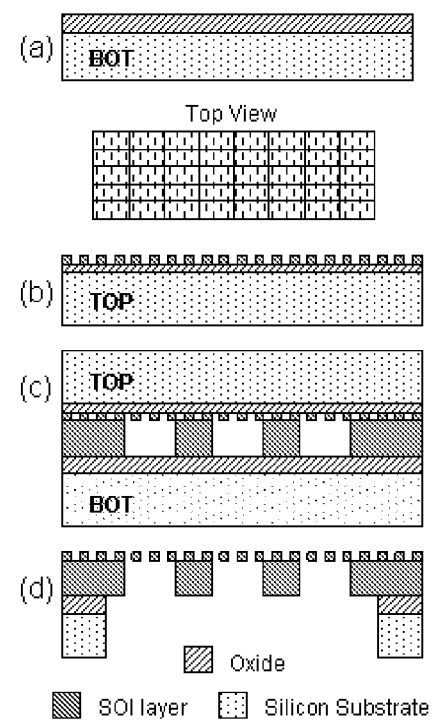
FIG. 16 shows an exemplary membrane manufacture method in some embodiments of the present invention.

Two distinct SOI wafers are used to achieve high-density and rigid membranes (FIG. 16). FIG. 16 shows a cross-sectional fabrication sequence utilizing two SOI wafers: (a) bottom wafer SOI layer is patterned and etched into a rectangular array using standard MEMS processes; (b) top wafer SOI layer is pattered using nanoimprint lithography and RIE; (c) the two wafers are fusion bonded together; (d) top substrate is removed, bottom substrate is patterned, and device is released by removing oxide from the backside and the pores are opened via a hydrofluoric acid etch. The membrane geometry and layer thickness values are representative values to convey process capabilities. In some embodiments, the first wafer, designated "BOT" for bottom wafer, is a 400 µm-thick, double-side polished SOI wafer. The actual film thickness may be selected as desired. In some embodiments, the active layer is 10-15 µm thick and the buried oxide (BOX) is 1.0 µm thick. The first step is to pattern the SOI layer using standard photolithography and deep reactive ion etching (DRIE). The SOI layer will be patterned into crossbar patterns for optimal strength. The second wafer, designated "TOP" for top wafer, is a SmartCut™ SOI wafer with an active layer with thickness of 200-500 nm, while its BOX layer thickness is 200-300 nm. The silicon substrate is 400 µm thick.

The SOI layer of the top wafer can be patterned using nanoimprint lithography and RIE. Patterning of slit-patterns down to 10 nm-widths, for example, can be achieved via careful template fabrication (Leica Microsystems VB6UHR EWF) and process development (Molecular Imprints IMPRIO-100, MRC-UTexas). The resulting pattern in the SOI layer of the top wafer provides a high-density pattern comprising arrays of spaces as small as, for example, 10 nm-wide (and up to 50 nm) with 50 nm separation. In the next step, the two wafers are bonded together using silicon-to-silicon fusion bonding. Afterwards, the top wafer substrate is removed using XeF$_2$ etching and the bottom wafer substrate is patterned using photolithography and DRIE. The final step of the fabrication process is to release the membranes by selectively etching the oxide layers in hydrofluoric acid.

In some embodiments, to avoid oxidation problems or limitations on lithography techniques, different pore designs are employed to achieve similar results. For example, in some embodiments, the design increases the separation of slit pores to 100 nm, while decreasing membrane thickness to 500 nm. It is contemplated that this design maintains desired hydraulic permeability. In some embodiments, the design approach involves patterning 50 nm-wide pores followed by thermal oxidation of sidewalls.

In some embodiments, the target design for the hemofilter is a 0.5 µm-thick membrane with arrays of <10 nm-wide slit pores with 100 nm separation. In some embodiments, such membrane geometry and nanopore arrangement achieves 30 ml/min filtration rate with 30 mmHg of transmembrane pressure within an overall membrane area of 0.1 m2. The choice of the 10 nm as maximum is derived from existing high-flux polysulfone hemodialysis membranes, which are rated with a mean pore size typically at 3-5 nm (see, e.g., Bowry, S. K., Int. J. Artif. Organs 2002, 25(5), page 447). In some embodiments, a closer nanopore spacing in a 0.5 μm-thick membrane (see, FIG. 17) is achieved. In some embodiments, single crystal silicon is used instead of polysilicon, for the first structural layer to avoid grain boundary effects for <10 nm-thick oxide film growth.

Example 13

This example shows that membranes having slit shaped nanofabricated pores offer enhanced selectivity in comparison to membranes having round shaped nanofabricated pores. In experiments conducted during the course of development of embodiments for the present invention, membranes having slit shaped nanofabricated pores in comparison to membranes having round shaped nanofabricated pores were shown to having enhanced clearance of middle-molecular weight toxins while still retaining albumin.

All publications and patents mentioned in the above specification are herein incorporated by reference in their entireties. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. An ultrafiltration system comprising:
a) a membrane consisting of a plurality of nanofabricated slit shaped pores having a width less than 20 nanometers, wherein said plurality of nanofabricated slit shaped pores are arranged in a rectangular configuration on said membrane, wherein said rectangular configuration is at least a 2:1 arrangement of said nanofabricated slit shaped pores on said membrane, wherein said nanofabricated slit shaped pores are arranged in the center of said membrane, wherein the distance between said nanofabricated slit shaped pores on said membrane is around 50 nm, wherein the thickness of the membrane is approximately 500 nm, wherein the membrane has a porosity around 20%;
b) a housing containing said membrane; and
c) a fluid delivery passageway with a first end and a second end, said first end positioned outside of said housing, said second end positioned to deliver fluid across said membrane.

2. The system of claim 1, wherein said fluid is delivered across said membrane via perfusion pressure.

3. The system of claim 1, further comprising a pump configured to deliver said fluid across said membrane.

4. The system of claim 1, further comprising an actuator configured to decrease protein fouling of said nanofabricated pores.

5. The system of claim 1, further comprising a control component used to control/monitor extracellular fluid volume.

6. The system of claim 1, wherein the length of said nanofabricated pores is less than 50 μm.

7. The system of claim 1, wherein said housing comprises a coating, said coating being biocompatible for in vivo use.

8. The system of claim 1, wherein said system further comprises one or more electrodes positioned on or near said membrane such that an electric field is generated in or near said pores.

9. The system of claim 1, wherein said housing has a length and a width, said length of said housing being less than 300 millimeters and said width of said housing being less than 300 millimeters.

10. The system of claim 1, wherein said membrane has a surface coating selected from the group consisting of polyethylene glycol, oligosaccharide surfactant polymers, heparin, and hyaluronan.

11. The system of claim 1, wherein the material of said membrane is selected from the group consisting of silicon, polysilicon, silicon carbide, ultrananocrystalline diamond, diamond-like-carbond (DLC), silicon dioxide, PMMA, SU-8, PTFE, titanium, silica, silicon nitride, polytetrafluorethylene, polymethylmethacrylate, polystyrene, and silicone.

12. An ultrafiltration system comprising:
a) a membrane consisting of a plurality of nanofabricated slit shaped pores having a width less than 20 nanometers, wherein said plurality of nanofabricated slit shaped pores are arranged in a rectangular configuration on said membrane, wherein said rectangular configuration is at least a 2:1 arrangement of said nanofabricated slit shaped pores on said membrane, wherein said nanofabricated slit shaped pores are arranged in the center of said membrane, wherein the distance between said nanofabricated slit shaped pores on said membrane is around 50 nm, wherein the thickness of the membrane is approximately 500 nm, wherein the membrane has a porosity around 20%, wherein said membrane has a surface coating selected from the group consisting of polyethylene glycol, oligosaccharide surfactant polymers, heparin, and hyaluronan;
b) a housing containing said membrane; and
c) a fluid delivery passageway with a first end and a second end, said first end positioned outside of said housing, said second end positioned to deliver fluid across said membrane.

13. The system of claim 12, wherein said fluid is delivered across said membrane via perfusion pressure.

14. The system of claim 12, further comprising a pump configured to deliver said fluid across said membrane.

15. The system of claim 12, further comprising an actuator configured to decrease protein fouling of said nanofabricated pores.

16. The system of claim 12, further comprising a control component used to control/monitor extracellular fluid volume.

17. The system of claim 12, said plurality of nanofabricated pores having a width less than 20 nanometers.

18. The system of claim 12, wherein the length of said nanofabricated pores is less than 50 μm.

19. The system of claim 12, wherein said housing comprises a coating, said coating being biocompatible for in vivo use.

20. The system of claim 12, wherein said system further comprises one or more electrodes positioned on or near said membrane such that an electric field is generated in or near said pores.

21. The system of claim 12, wherein said housing has a length and a width, said length of said housing being less than 300 millimeters and said width of said housing being less than 300 millimeters.

22. The system of claim 12, wherein the material of said membrane is selected from the group consisting of silicon, polysilicon, silicon carbide, ultrananocrystalline diamond, diamond-like-carbond (DLC), silicon dioxide, PMMA, SU-8, PTFE, titanium, silica, silicon nitride, polytetrafluorethylene, polymethylmethacrylate, polystyrene, and silicone.

23. An ultrafiltration system comprising:
   a) a membrane consisting of a plurality of nanofabricated slit shaped pores having a width less than 20 nanometers, wherein said plurality of nanofabricated slit shaped pores are arranged in a rectangular configuration on said membrane, wherein said rectangular configuration is at least a 2:1 arrangement of said nanofabricated slit shaped pores on said membrane, wherein the distance between said nanofabricated slit shaped pores on said membrane is around 50 nm, wherein the thickness of the membrane is approximately 500 nm, wherein the membrane has a porosity around 20%, wherein said nanofabricated slit shaped pores are arranged in the center of said membrane; said membrane having a surface coating selected from the group consisting of polyethylene glycol, oligosaccharide surfactant polymers, heparin, and hyaluronan;
   b) a housing containing said membrane and said electrode; and
   c) a fluid delivery passageway with a first end and a second end, said first end positioned outside of said housing, said second end positioned to deliver fluid across said membrane.

24. The system of claim 23, wherein said fluid is delivered across said membrane via perfusion pressure.

25. The system of claim 23, further comprising a pump configured to deliver said fluid across said membrane.

26. The system of claim 23, further comprising an actuator configured to decrease protein fouling of said nanofabricated pores.

27. The system of claim 23, wherein the material of said membrane is selected from the group consisting of silicon, polysilicon, silicon carbide, ultrananocrystalline diamond, diamond-like-carbond (DLC), silicon dioxide, PMMA, SU-8, PTFE, titanium, silica, silicon nitride, polytetrafluorethylene, polymethylmethacrylate, polystyrene, and silicone.

28. The system of claim 23, further comprising a control component used to control/monitor extracellular fluid volume.

29. The system of claim 23, wherein the length of said nanofabricated pores is less than 50 μm.

30. The system of claim 23, wherein said housing comprises a coating, said coating being biocompatible for in vivo use.

31. The system of claim 23, wherein said system further comprises one or more electrodes positioned on or near said membrane such that an electric field is generated in or near said pores.

32. The system of claim 23, wherein said housing has a length and a width, said length of said housing being less than 300 millimeters and said width of said housing being less than 300 millimeters.

33. An implantable ultrafiltration device comprising:
   a) a membrane consisting of a plurality of nanofabricated slit shaped pores having a width less than 20 nanometers, wherein said plurality of nanofabricated slit shaped pores are arranged in a rectangular configuration on said membrane, wherein said rectangular configuration is at least a 2:1 arrangement of said nanofabricated slit shaped pores on said membrane, wherein said nanofabricated slit shaped pores are arranged in the center of said membrane, wherein the distance between said nanofabricated slit shaped pores on said membrane is around 50 nm, wherein the thickness of the membrane is approximately 500 nm, wherein the membrane has a porosity around 20%; said membrane having a surface coating selected from the group consisting of polyethylene glycol, oligosaccharide surfactant polymers, heparin, and hyaluronan;
   b) a biocompatible housing containing said membrane; and
   c) a fluid delivery passageway with a first end and a second end, said first end positioned outside of said housing, said second end positioned to delivery fluid across said membrane.

34. The device of claim 33, wherein said fluid is delivered across said membrane via perfusion pressure.

35. The device of claim 33, further comprising a pump configured to deliver said fluid across said membrane.

36. The device of claim 33, further comprising an actuator configured to decrease protein fouling of said nanofabricated pores.

37. The device of claim 33, further comprising a control component used to control/monitor extracellular fluid volume.

38. The device of claim 33, wherein the material of said membrane is selected from the group consisting of silicon, polysilicon, silicon carbide, ultrananocrystalline diamond, diamond-like-carbond (DLC), silicon dioxide, PMMA, SU-8, PTFE, titanium, silica, silicon nitride, polytetrafluorethylene, polymethylmethacrylate, polystyrene, and silicone.

39. The device of claim 33, wherein the length of said nanofabricated pores is less than 50 μm.

40. The device of claim 33, wherein said housing comprises a coating, said coating being biocompatible for in vivo use.

41. The device of claim 33, further comprising a population of cells attached to said membrane.

42. The device of claim 41, wherein said cells are selected from the group consisting of renal tubule cells, pancreatic cells, hepatic cells, thyroid cells, adrenal cells, parathyroid cells, pituitary cells, hypothalamic cells, gonadal cells, prokaryotic cells, duodenal cells, gastric cells, intestinal cells, muscle cells, fibroblast cells, and endothelial cells.

43. The device of claim 33, wherein said housing has physical dimensions that permit said device to be used in a human subject, in vivo.

44. The device of claim 33, further comprising one or more sensors associated with said membrane, wherein said sensor is configured to monitor filtration parameters.

45. The device of claim 44, wherein said one or more sensors are selected from the group consisting of a pressure sensor configured to monitor transmembrane pressure, a proteins sensor configured to monitor protein leakage/membrane breakdown, an optical blood sensor configured to monitor membrane rupture, and urea sensor configured to monitor urea clearance.

* * * * *